(12) United States Patent
Melin

(10) Patent No.: US 12,409,170 B2
(45) Date of Patent: *Sep. 9, 2025

(54) COMPOSITION COMPRISING COMBINATION OF RAPAMYCIN AND METFORMIN AND USE THEREOF FOR TREATING NEURODEGENERATIVE DISEASES

(71) Applicant: JMM Licensing LLC, Meadowbrook, PA (US)

(72) Inventor: Jeffrey M. Melin, Meadowbrook, PA (US)

(73) Assignee: IMM Licensing LLC, Meadowbrook, PA (US)

( * ) Notice: Subject to any disclaimer, the term of this patent is extended or adjusted under 35 U.S.C. 154(b) by 5 days.

This patent is subject to a terminal disclaimer.

(21) Appl. No.: 18/394,155

(22) Filed: Dec. 22, 2023

(65) Prior Publication Data

US 2024/0261269 A1     Aug. 8, 2024

Related U.S. Application Data

(63) Continuation of application No. 17/392,516, filed on Aug. 3, 2021, now Pat. No. 11,890,274, which is a continuation of application No. 16/931,133, filed on Jul. 16, 2020, now Pat. No. 11,141,409, which is a continuation of application No. 16/040,160, filed on Jul. 19, 2018, now Pat. No. 10,952,994, which is a continuation of application No. 15/828,926, filed on Dec. 1, 2017, now Pat. No. 10,925,862, which is a continuation of application No. 15/241,312, filed on Aug. 19, 2016, now Pat. No. 10,765,665.

(60) Provisional application No. 62/318,302, filed on Apr. 5, 2016, provisional application No. 62/259,384, filed on Nov. 24, 2015.

(51) Int. Cl.
| | | |
|---|---|---|
| *A61K 31/436* | (2006.01) | |
| *A61K 9/00* | (2006.01) | |
| *A61K 9/06* | (2006.01) | |
| *A61K 31/155* | (2006.01) | |
| *A61K 31/519* | (2006.01) | |
| *A61K 47/10* | (2017.01) | |

(52) U.S. Cl.
CPC .......... *A61K 31/436* (2013.01); *A61K 9/0014* (2013.01); *A61K 9/0087* (2013.01); *A61K 9/06* (2013.01); *A61K 31/155* (2013.01); *A61K 31/519* (2013.01); *A61K 47/10* (2013.01); *A61K 2300/00* (2013.01)

(58) Field of Classification Search
CPC .................................................. A61K 31/436
See application file for complete search history.

(56) References Cited

U.S. PATENT DOCUMENTS

| | | |
|---|---|---|
| 5,100,899 A | 3/1992 | Calne |
| 5,362,718 A | 11/1994 | Skotnicki et al. |
| 5,540,931 A | 7/1996 | Hewitt et al. |
| 7,169,594 B2 | 1/2007 | Guan |
| 7,799,782 B2 | 9/2010 | Munson et al. |
| 8,026,276 B2 | 9/2011 | Rubino et al. |
| 8,150,592 B2 | 4/2012 | Song et al. |
| 8,197,804 B2 | 6/2012 | Sing et al. |
| 8,299,116 B2 | 10/2012 | Rubino et al. |
| 8,455,539 B2 | 6/2013 | Rubino et al. |
| RE44,768 E | 2/2014 | Skotnicki et al. |
| 8,722,700 B2 | 5/2014 | Rubino |
| 8,791,097 B2 | 7/2014 | Dukart et al. |
| 8,911,768 B2 | 12/2014 | Whitcup et al. |
| 8,911,786 B2 | 12/2014 | Desai et al. |
| 9,150,592 B2 | 10/2015 | Cusack et al. |
| 9,155,801 B2 | 10/2015 | Weisbart |
| 10,765,665 B2 | 9/2020 | Melin |
| 10,925,862 B2* | 2/2021 | Melin ............. A61P 37/06 |
| 10,952,994 B2* | 3/2021 | Melin ............. A61K 31/155 |
| 11,141,409 B2 | 10/2021 | Melin |
| 11,890,274 B2 | 2/2024 | Melin |
| 2006/0286046 A1 | 12/2006 | Haber |
| 2011/0144143 A1 | 6/2011 | Sun et al. |
| 2011/0256130 A1 | 10/2011 | Schultz et al. |
| 2011/0275597 A1 | 11/2011 | Namdeo et al. |
| 2012/0022095 A1 | 1/2012 | Teng et al. |
| 2012/0283332 A1 | 11/2012 | Scarbrough et al. |

(Continued)

FOREIGN PATENT DOCUMENTS

| | | |
|---|---|---|
| JP | 2011-529860 A | 12/2011 |
| JP | 2012-514633 A | 6/2012 |

(Continued)

OTHER PUBLICATIONS

Barrett, D. et al.; Targeting the PI3K/AKT/mTOR Signaling Axis in Children with Hematologic Malignancies; NIH Public Access Author Manuscript; Oct. 1, 2012; pp. 1-31; 14(5); Springer International Publishing.

(Continued)

*Primary Examiner* — Rei Tsang Shiao
(74) *Attorney, Agent, or Firm* — Hamilton, Brook, Smith & Reynolds, P.C.

(57) ABSTRACT

A formulation for treating neurodegenerative diseases comprising a combination of rapamycin and metformin in a molar ratio of about 20:1, 10:1, 5:1, 4:1, 3:1, or 1:1. A method of treating neurodegenerative diseases comprising administering the formulation comprising a combination of rapamycin and metformin in a molar ratio of about 20:1, 10:1, 5:1, 4:1, 3:1, or 1:1.

17 Claims, 4 Drawing Sheets

(56) References Cited

U.S. PATENT DOCUMENTS

| | | |
|---|---|---|
| 2014/0186306 A1 | 7/2014 | Plante |
| 2014/0301980 A1 | 10/2014 | Day |
| 2017/0143682 A1 | 5/2017 | Melin |
| 2018/0153864 A1 | 6/2018 | Melin |
| 2019/0000815 A1 | 1/2019 | Melin |
| 2020/0345703 A1 | 11/2020 | Melin |
| 2021/0361630 A1 | 11/2021 | Melin |

FOREIGN PATENT DOCUMENTS

| | | |
|---|---|---|
| JP | 2012-131827 | 7/2012 |
| WO | WO 2008/022256 | 2/2008 |
| WO | WO 2008/110491 | 9/2008 |
| WO | WO 2010/028596 A1 | 3/2010 |
| WO | WO 2010/073642 A1 | 7/2010 |
| WO | WO 2014/052640 A1 | 4/2014 |
| WO | WO 2017/034315 A1 | 3/2017 |
| WO | WO 2017/091454 A1 | 6/2017 |

OTHER PUBLICATIONS

Bhattaram, P. et al.; "Inflammatory Cytokines Stabilize SOXC Transcription Factors to Mediate the Transformation of Fibroblast-Like Synoviocytes in Arthritic Disease," Arthritis & Rheumatology, vol. 70, No. 3, Mar. 2018, pp. 371-382.

Bibee, K.P., et al.; Rapamycin Nonoparticles Target Defective Autophagy in Muscular Dystrophy to Enhance Both Strength and Cardiac Function; The FASEB Journal—Research Communication; May 2014; pp. 2047-2061; vol. 28.

Bride, K. et al.; Sirolimus is Effective for Autoimmune Cytopenias; Blood First Edition Paper; Oct. 26, 2015; pp. 1-35; American Society of Hematology.

Bruyere et al. "A consensus statement on the European Society for Clinical and Economic Aspects of Osteoporosis and Osteoarthritis (ESCEO) algorithm for the management of knee osteoarthritis—From evidence-based medicine to the to the real-life setting," Seminars in Arthritis and Rheumatism, 2015, 9 pages, published by Elsevier HS Journals, Inc.

Bruyn, G et al.; Everolimus in Patients with Rheumatoid Arthritis Receiving Concomitant Methotrexate: a 3-month, Double-blind, Randomised, Placebo-Controlled, Parallel-group, proof-of-concept Study; http://ard.bmj.com/content/67/8/1090; 2008; pp. 1-5; vol. 67, Issue 8; BMJ Publishing Group and European League Against Rheumatism.

Bubna; Indian J. Pharmacol., 2016, vol. 48, No. 1, pp. 4-10 (Year: 2016).

Cejka, et al.; Arthritis & Rheumatism, 2010, vol. 62, No. 8, pp. 2294-2302 (Year: 2010).

Checkley, L.A. et al.; Metromin Inhibits Skin Tumor Promotion in Overweight and Obese Mice; Cancer Prevention Research; Nov. 6, 2013; pp. 54-65; 7(1); American Association for Cancer Research.

Checkley et al. "Metformin Inhibits Skin Tumor Promotion in Overweight and Obese Mice," Cancer Prevention Research, vol. 7, No. 1, Nov. 6, 2013, pp. 54-64 XP055332804, United States.

Efe, et al. "Penetration of topical diclofenac sodium 4% spray gel into the synovial tissue and synovial fluid of the knee: a randomised clinical trial," Knee Surg sports Traumatol Arthrosc (2014) 22:345-350, published by Springer-Verlag Berlin Heidelberg 2013.

Haemel, et al. "Topical Rapamycin; a Novel Approach to Facial Angiofibromas in Tuberous Sclerosis," Arch Dermatol, vol. 146, No. 7, Jul. 2010, published by American Medical Association 2010.

Intravitreal Sirolimus as Therapeutic Approach to Uveitis—Full Text View—ClinicalTrials.gov (date unavailable).

Kloppenburg, et al. "2018 update of the EULAR recommendations for the management of hand osteoarthritis," Ann Rheum Dis, 0:1-9, 2018, doi: 10.1136/annrheumdis-2018-213826.

Lai, Z. et al.; N-Acetylcysteine Reduces Disease Activity by Blocking MTOR in T Cells of Lupus Patients; NIH Public Access Author Manuscript; Sep. 2012; pp. 1-15; 64(9).

Lamming, D. et al.; Rapalogs and MTOR Inhibitors as Anti-aging Therapeutics; The Journal of Clinical Investigation; Mar. 2013; pp. 980-989; vol. 123, No. 3.

MacKenzie, M.J. et al., "A phase I study of temsirolimus and metformin in advanced solid tumours," Invest New Drugs, vol. 30; No. 2; 647-652 (2012).

Madke, Indian Dermatol. Online J. 2013, vol. 4, No. 1, pp. 54-57 (Year: 2013).

Mahalati, K. and Kahan, B.D., "Clinical Pharmacokinetics of Sirolimus," Clin. Pharmacokinet., vol. 40; 573-585 (2001).

Marques et al. "Topical rapamycin combined with pulsed dye laser in the treatment of capillary vascular malformations in Sturge-Weber syndrome: Phase II, randomized, double-blind, intraindividual placebo-controlled clinical trial," Nov. 11, 2014, published by the American Academy of Dermatology, Inc., 2014.

Mayo Clinic, ClinicaiTrials.gov NCT01649960, posted Jul. 25, 2012 (Year: 2012).

Mayo Clinic; "Arthritis pain: Treatments absorbed through your skin", https://www.mayoclinic.org/diseases-conditions/osteoarthritis/in-depth/pain-maedications/art-20045899, accessed Feb. 21, 2018.

Mekahli, D. et al., "Polycystin-1 but not polycystin-2 deficiency causes upregulation of the mTOR pathway and can be synergistically targeted with rapamycin and metformin", Eur. J. Physiol., vol. 466, 1591-1604 (2014).

Metformin Dosage, Life Extension, Aug. 2003, https://www.lifeextension.com/Featured%20Articles/2003/8/Metformin%20Dosage/Page%2001 (Year: 2003).

Migata et al., Clin. Exp. Immunol., 1996, vol. 104, pp. 86-91 (Year: 1996).

Miyatake, S. et al.; "Randomized clinical comparisons of diclofenac concentration in the soft tissues and blood plasma between topical and oral applications," British Journal of Clinical Pharmacology, 67:1, pp. 125-129 (date unavailable).

Naing, Exp. Op. Invest. Drugs, 2013, vol. 22, No. 6, pp. 679-685 (Year: 2013).

Oy, S.; Public Summary of Opinion on Orphan Designation Sirolimus for the Treatment of Chronic Non-infectious Uveitis; Sep. 20, 2011; pp. 1-4; European Medicines Agency; United Kingdom.

Phillips, B. et al.; A Retrospective Review of Oral Low-dose Sirolimus (rapamycin) for the Treatment of Active Uveitis; J Ophthal Inflamm Infect; 2011; pp. 29-34; 1; The Authors.

Rannou, et al. "Efficacy and safety of topical NSAIDs in the management of osteoarthritis: Evidence from real-life setting trials and surveys," Seminars in Arthritis and Rheumatism, 2016, 4 pages, published by Elsevier HS Journals, Inc.

Riaz, H. et al.; mTOR Inhibitors: A Novel Class of Anti-Cancer Agents; Infectious Agents and Cancer; 2012; pp. 1-2; 7:1; BioMed Central.

Saha, A. et al., "Effect of Metformin, Rapamycin, and their Combination on Growth and Progression of Prostate Tumors in HiMyc Mice," Cancer Prevention Research, vol. 8, No. 7, 597-606 (2015).

Son et al. "Modulators of Inflammation," 2014, Article ID 973986 (Year 2014).

Teachey, D. et al.; mTOR Inhibitors are Synergistic with Methotreazate; An Effective Combination to Treat Acute Lymphoblastic Leukemia; Bloodjournal.org; Sep. 1, 2008; pp. 2020-2024; vol. 112, No. 5; Blood.

Wee, J. S., et al.; Familial Multiple Discoid Fibromas: Unique Histological Features and Therapeutic Response to Toical Rapamycin; British Journal of Dermatology; 2013; pp. 177-180; The Authors and British Association of Dermatologists.

Yan, H. et al.; Suppression of Experimental Arthritis Through AMP-activated Protein Kinase Activation and Autophagy Modulation; HHS Public Access Author Manuscript; Feb. 28, 2015; pp. 1-18; 1(1): 5-.

You, S. et al.; "The Tumor-Like Phenotype of Rheumatoid Synovium: Molecular Profiling and Prospects for Precision Medicine," Arthritis & Rheumatology; vol. 70, No. 5, May 2018, pp. 637-652.

Yu et al., J. Gerontal. A Biol. Sci. Med. Sci., 2015, vol. 70, No. 4, pp. 410-420 (Year: 2015).

Yu, G. et al.; Metformin Potentiates Rapamycin and Cisplatin in Gastric Cancer in Mice; www.impactjournals.com/oncotarget/; Feb. 28, 2015; pp. 12748-12762; vol. 6, No. 14.

(56) References Cited

OTHER PUBLICATIONS

Extended European Search Report and Written Opinion received for EP Patent Application No. 21187553.9, mailed on Nov. 5, 2021, 11 pages.
International Preliminary Report on Patentability received for PCT Patent Application No. PCT/US16/62656, mailed on Jun. 7, 2018, 8 pages.
Examination Report issued by the European Patent Office for Patent Application No. 16 805 683.6-1109 dated May 17, 2021, 10 pages.
Examination Report issued by the European Patent Office for Patent Application No. 16 805 683.6-1109 dated Nov. 25, 2019, 11 pages.
International Search Report of the International Searching Authority for International Patent Application No. PCT/US2016/062656 dated Jan. 13, 2017, 5 pages.
Office Action/Notice of Reasons for Rejection issued by the Japanese Patent Office for Japanese Patent Application No. 2018-527959 dated Aug. 4, 2020, 8 pages.
Written Opinion of the International Searching Authority for International Patent Application No. PCT/US2016/062656 dated Jan. 13, 2017, 7 pages.
Non-Final Office Action for U.S. Appl. No. 17/392,516, mailed Jul. 26, 2023.
Notice of Allowance for U.S. Appl. No. 17/392,516, mailed Dec. 14, 2023.
International Search Report and Written Opinion received for PCT Patent Application No. PCT/US16/62656, mailed on Jan. 13, 2017, 10 pages.

\* cited by examiner

COMPOSITION COMPRISING COMBINATION OF RAPAMYCIN AND METFORMIN AND USE THEREOF FOR TREATING NEURODEGENERATIVE DISEASES

RELATED APPLICATIONS

This application is a Continuation of U.S. application Ser. No. 17/392,516, filed on Aug. 3, 2021, which is a continuation of U.S. application Ser. No. 16/931,133 filed on Jul. 16, 2020, now U.S. Pat. No. 11,141,409, which is a Continuation of U.S. application Ser. No. 16/040,160, now U.S. Pat. No. 10,952,994, filed on Jul. 19, 2018, which is a continuation of U.S. application Ser. No. 15/828,926, now U.S. Pat. No. 10,925,862, filed on Dec. 1, 2017, which is a continuation of U.S. application Ser. No. 15/241,312, now U.S. Pat. No. 10,765,665, filed on Aug. 19, 2016, which claims the benefit of U.S. Provisional Application No. 62/259,384 filed on Nov. 24, 2015 and U.S. Provisional Application No. 62/318,302 filed on Apr. 5, 2016. The entire teachings of the above applications are incorporated herein by reference.

FIELD OF THE INVENTION

This invention relates to a composition comprising a combination of rapamycin and an activator of AMP kinase for use in the treatment and/or prevention of diseases and disease conditions. The invention also relates to methods of treating and/or preventing diseases and disease conditions.

BACKGROUND

Rapamycin (marketed as sirolimus)) is a macrolide produced by the bacterium *Streptomyces hygroscopicus*. Sirolimus is currently used as an immunosuppressant and is most often used to prevent rejection of transplanted organs. Sirolimus has two approved indications—renal transplantation and lymphangioleiomyomatosis (LAM). Rapamycin has also been shown to be potentially effective in treating Tuberous Sclerosis Complex (TSC)-associated seizures, skin disease, brain lesions, pulmonary lesions, and renal lesions. Because rapamycin is an immunosuppressant, long-term (chronic) use of the drug may increase a patient's risk for developing serious side effects (such as infection and pulmonary toxicity). These findings have raised safety concerns about the suitability of rapamycin for long-term use.

Rapamycin is an inhibitor of mTOR complex 1 (mTORC1). mTOR (mammalian target of rapamycin) is a serine threonine kinase and is a master regulator of protein synthesis, cell growth, and cell metabolism. Excessive mTORC1 activity has been implicated in multiple disease conditions including tuberous sclerosis complex (TSC); polyhydramnios, megalencephaly, and symptomatic epilepsy (PMSE) syndrome; various cancers including breast, colon, kidney, lung, prostate, pancreatic, etc., inflammatory bowel disease, inflammatory arthritides (multiple types), inflammatory skin diseases (multiple types), Systemic Lupus Erythematosis, and neurodegenerative diseases (including Alzheimer's Disease).

Several studies have indicated that rapamycin may be used to treat or prevent some disease conditions by inhibiting the mTORC1 pathway. Approved rapalogs at current labeling and posology, however, have significant safety issues with a risk benefit profile considered inappropriate for use in patients without an advanced malignancy, organ transplant, or tuberous sclerosis complex.

Thus, there remains a need for safe and effective treatment utilizing rapalogs for these and other non-malignant conditions.

The present drug combination results in increased efficacy without increasing dosage amounts or frequency of doses of rapamycin

SUMMARY

In one aspect, the invention relates to a composition comprising a combination of rapamycin and an activator of AMP kinase for use in the treatment and/or prevention of diseases and disease conditions. In one embodiment, the AMP kinase activator is metformin.

In one embodiment the composition is a topical formulation. The topical formulation may be a gel, an ointment, a cream, or a lotion. In one embodiment, the topical formulation may include a molar ratio of rapamycin to metformin in the range of about 20:1 to about 1:1; about 20:1 to about 3:1; about 20:1 to about 4:1; about 20:1 to about 5:1; about 15:1 to about 1:1, about 15:1 to about 3:1; about 15:1 to about 4:1; about 15:1 to about 5:1; about 10:1 to about 3:1; about 10:1 to about 4:1; about 10:1 to about 5:1; about 5:1 to about 4:1; about 5:1 to about 3:1; or about 5:1 to about 1:1.

In another aspect, the invention relates to methods of treating and/or preventing diseases and disease conditions.

In one embodiment, the method is a method for treating a joint disease in a subject, wherein the joint disease is characterized by inflammation. The method comprises administering an effective amount of a topical formulation directly over or on top of an inflamed or diseased joint affected by the joint disease. The topical formulation comprises a combination of rapamycin and metformin. In one embodiment the topical formulation may include a molar ratio of rapamycin to metformin in the range of about 20:1 to about 1:1; about 20:1 to about 3:1; about 20:1 to about 4:1; about 20:1 to about 5:1; about 15:1 to about 1:1, about 15:1 to about 3:1; about 15:1 to about 4:1; about 15:1 to about 5:1; about 10:1 to about 3:1; about 10:1 to about 4:1; about 10:1 to about 5:1; about 5:1 to about 4:1; about 5:1 to about 3:1; or about 5:1 to about 1:1.

In one embodiment, the topical formulation may be selected from a gel, an ointment, a cream, or a lotion.

In one embodiment, the joint disease is an inflammatory arthritis. In one embodiment, the inflammatory arthritis is osteoarthritis.

In one embodiment, the method is a method for treating an inflammatory skin disease in a subject. The method comprises administering an effective amount of a topical formulation directly to an area of skin affected by the inflammatory skin disease, the topical composition comprising a combination of rapamycin and metformin, wherein the molar ratio of rapamycin to metformin is in the range of about 20:1 to about 4:1.

In one embodiment, the molar ratio of rapamycin to metformin is in the range of about 20:1 to about 1:1; about 20:1 to about 3:1; about 20:1 to about 4:1; about 20:1 to about 5:1; about 15:1 to about 1:1, about 15:1 to about 3:1; about 15:1 to about 4:1; about 15:1 to about 5:1; about 10:1 to about 3:1; about 10:1 to about 4:1; about 10:1 to about 5:1; about 5:1 to about 4:1; about 5:1 to about 3:1; or about 5:1 to about 1:1.

In one embodiment, the inflammatory skin disease may be atopic dermatitis (eczema).

In one embodiment, the method is a method of treating an autoimmune inflammatory skin disease. The autoimmune inflammatory disease may be associated with systemic lupus erythematosus or discoid lupus erythematosus.

DETAILED DESCRIPTION

Figure 1:
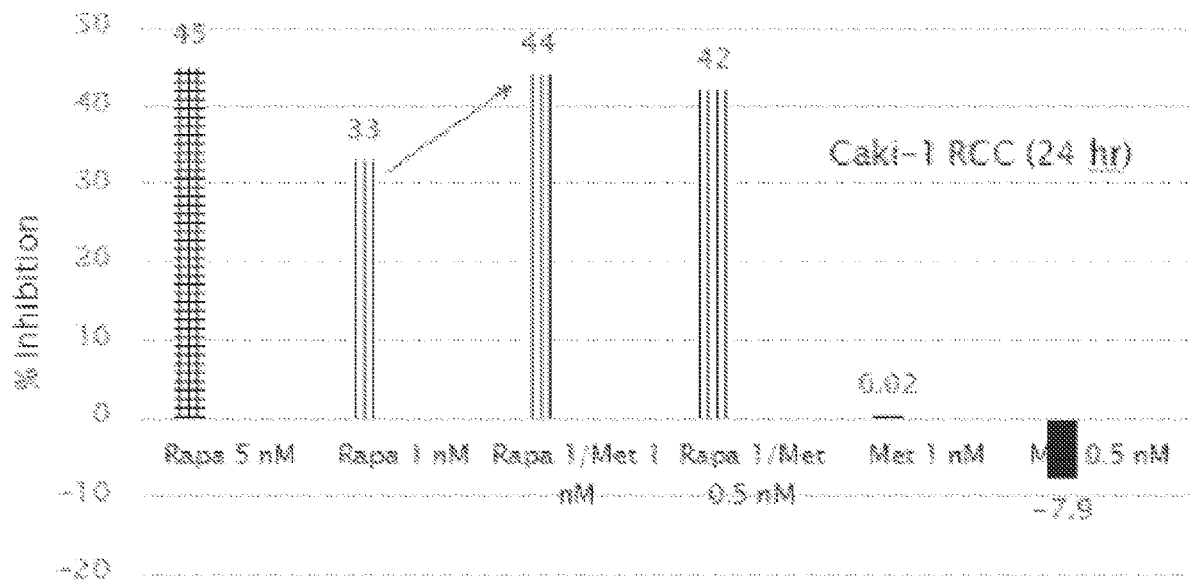
FIG. 1 is a bar graph depicting the percent inhibition of $^3$H-uptake of different doses of rapamycin and metformin alone or in combination in Caki-1 renal carcinoma cells and shows that substandard doses of metformin potentiate rapamycin at 1 nM.

As used herein, approximating language may be applied to modify any quantitative representation that may vary without resulting in a change in the basic function to which it is related. Accordingly, a value modified by a term or terms, such as "about" and "substantially," may not to be limited to the precise value specified, in some cases.

Rapamycin works by inhibiting the mTORC1 enzyme pathway. This pathway is responsible for many key cellular processes involved in multiple diseases, including autophagy, HIF-1alpha and VEGF production, cell growth, and adaptive immunity. While rapamycin is a frequently used drug for renal transplant patients, long-term use of rapamycin at standard (typically high) doses can have significant deleterious health effects.

According to one aspect of the invention, the combination of rapamycin with an enhancing agent augments efficacy and lowers the risk from unwanted side effects due to excessive rapamycin dosing. Applicant has discovered a complementary agent that acts through an alternative pathway to enhance the efficacy of rapamycin when used alone (i.e., as monotherapy) for a variety of neoplastic and non-neoplastic diseases, especially when administered topically or locally in a tissue-targeted, site-specific fashion.

By studying the mTORC1 pathway, it was noted that upstream enhancement of an earlier pathway involving the enzyme AMPK (before mTORC1 becomes active) could enhance the effect of rapamycin within the cell. Multiple compounds have been found to activate AMPK. For example, a metabolite of adenosine called AICA riboside indirectly inhibits mTORC1 through a series of upstream events that involve activation of AMPK. Methotrexate (MTX) increases intracellular concentrations of molecules that activate AMPK such as AICA riboside (5-aminoimidazole-4-carboxamide riboside), AICAR, and ZMP (aminoimidazole carboxamide ribonucleotide). Activated AMPK in turn inhibits mTORC1 through at least two discrete pathways.

Metformin, a widely used drug for the first-line treatment of type 2 diabetes, indirectly activates AMPK by inhibiting Complex I of the mitochondrial respiratory chain. Metformin inhibits ATP synthesis and, thus, increases intracellular levels of ADP and AMP (which leads to activation of AMPK via LKB1 activation).

Multiple additional compounds have been found to activate AMPK. One of these is Permetrexed, an anti-folate drug indicated for non-small cell lung cancer and mesothelioma. Permetrexed inhibits the enzyme aminoimidazole carboxamide ribonucleotide formyltransferase (AICART), which in turn leads to the accumulation of AMP, and activation of AMPK.

Without being bound by any specific theory, metformin suppresses mTORC1 signaling through both AMPK-dependent and AMPK-independent mechanisms. Because of this upstream series of enzymatic reactions, combining into a single formulation non-standard (e.g., lower than typically prescribed) doses of rapamycin with an AMPK activator (also at non-standard lower doses than is typically prescribed)) may potentiate mTORC1 inhibition.

In one embodiment of the invention, the composition comprises a combination of rapamycin with metformin or another activator of AMPK (for example, methotrexate) to enhance efficacy with respect to mTORC1 inhibition, as well as allow for any complementary non-redundant salutary effects. This combination may be used in the treatment of rheumatologic, neurodegenerative, and heritable and inborn genetic diseases, especially when administered topically or locally in a tissue-targeted, site-specific fashion.

The popular belief has always been that the mechanism of action (MOA) of methotrexate is through inhibition of purine metabolism through inhibition of dihydrofolate reductase (DHFR). Teachcy, et al (Blood (2008)112(5):220-23) was the first to suggest synergy between methotrexate and rapamycin in a non-clinical murine/ex-vivo study of human Acute Lymphoblastic Leukemia (ALL) cells lines. Teachey et al. hypothesized that the MOA of methotrexate is through an upstream effect of inhibiting DHFR activity rather than enhancement of mTOR inhibition. Teachey et al. state that "because resistance to MTX may correlate with high DHFR expression, we hypothesized mTOR inhibitors may increase sensitivity of ALL to MTX through decreasing DHFR by increasing turnover of cyclin D."

Recognition of the alternative intracellular mechanism of action through mTOR is crucial in the discovery that methotrexate would be an additive or synergistic agent with rapamycin and therapeutically important. A combination drug comprising both rapamycin and methotrexate (or metformin) in a single dosage form is unknown. It is also unknown that the drugs in combination act as a more efficacious mTORC1 inhibitor than either drug alone or whether this combination is even safe (i.e., does not result in serious dose-limiting toxicity when used long-term). This combination product could be more efficacious than either drug alone and may result in improvement in safety by allowing for lower doses of rapamycin to be used chronically, especially when administered topically or locally in a tissue-targeted, site-specific fashion.

One aspect of the invention provides a drug combination comprising rapamycin and any activator of AMP kinase. In one embodiment, the AMP kinase (AMPK) activator may be chosen from compounds such as: methotrexate; metformin; phenformin, a thiazolidinedione; a salicylate; a plant product (e.g., resveratrol from red wine, epigallocatechin-3-gallate from green tea, berberine); AICA riboside; AICAR (5aminoimidazole-4-carboxamide ribonucleotide); or a combination of two or more thereof. In one embodiment, the AMPK activator is methotrexate. In another embodiment, the AMPK activator is metformin.

The combination of low (non-standard) dose rapamycin and methotrexate may be most effective at treating autoimmune and immunologically mediated inflammatory disorders, while the combination of rapamycin and metformin may be most effective for patients with diabetes, metabolic syndrome, and obesity. The combination of rapamycin and metformin may also be more effective for Alzheimer's disease and other protein deposition-associated neurodegenerative diseases, as well as diabetic retinopathy, age-related macular degeneration, osteoarthritis associated with type 2 diabetes, chronic liver diseases (including non-alcoholic steatohepatitis and autoimmune liver diseases, other autoimmune disorders, chronic non-autoimmune inflammatory disorders, heritable and inborn genetic diseases associated with high mTORC1 activation states, primary and secondary chemoprevention of both malignant and non-malignant neoplasms, cancer treatment, and chronic pain associated with inflammatory diseases. In one embodiment, the chronic pain is associated with inflammatory arthritis, e.g., osteoarthritis.

Rapamycin is a macrolide produced by the bacterium *Streptomyces hygroscopicus* having the chemical formula:

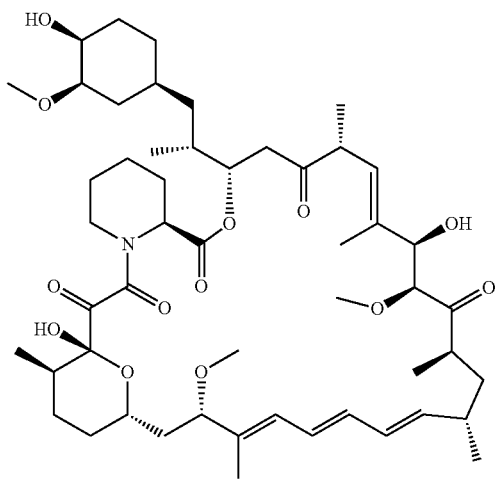 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@H](O)[C@H](OC)C2)CC(=O)[C@H](C)/C=C(\C)[C@@H](O)[C@H](OC)C(=O)[C@H](C)C[C@H](C)/C=C/C=C/C=C/1C]

In one embodiment, a chemical analog of rapamycin, known as a rapalog, may be used in place of rapamycin. Potentially suitable rapalogs include everolimus (Novartis, Afinitor®) and temsirolimus (Wyeth, Torisel®) as well as still yet to be approved mTORC1 inhibitors (such as ridaforolimus (Deforolimus)). As these rapalogs are all derivatives of rapamycin, it is preferred to use rapamycin.

In one embodiment, a newer second generation rapalog (such as Torin 1, KU0063794, OSE-027) may be used in place of rapamycin. These second generation rapalogs may more potently inhibit mTORC2 as well as mTORC1.

In another embodiment, the agent may inhibit mTORC1, mTORC2, or a combination of both mTORC1 and mTORC2. In yet another embodiment, the composition may include an agent that also inhibits other kinases, such as PI3K, may be used in place of rapamycin (such as NVP-BEZ235, GSK2126458, or PF-04691502) (known collectively as Dual PI3K/mTOR inhibitors).

In another embodiment, a rapalog (with or without an AMPK activator such as metformin) could be combined with an AKT inhibitor (such as AZD5363, GSK690693, Perifosine, and GDC-0068) or a PI3K inhibitor (such as idelalisib, buparlisib, wortmannin, GSK2636771, or GDC-0980[RG7422]).

In one embodiment, the drug combination comprises rapamycin and metformin. Metformin is a well-known drug commonly used as first-line treatment of type 2 diabetes mellitus, in addition to being used for polycystic ovary disease, metabolic syndrome, and diabetes prevention. The chemical name is 1,1-Dimethylbiguanide The structural formula is:

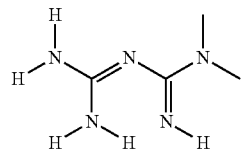

Use of such a drug combination may substantially reduce the amount of both rapamycin and metformin needed for successful treatment of diseases characterized by high mTOR activation states, when compared to use of either drug alone. Metformin can indirectly inhibit mTORC1 through direct activation of AMPK, but also can more directly inactivate mTORC1 through inactivating the Ragulator Complex (RagGTPase) and upregulate REDD1 (an mTORC1 inactivator). Metformin activates AMPK, which in turn directly inactivates mTORC1 (by phosphorylating Raptor), and also activates TSC2 (an mTORC1 inactivator (via Rheb) and tumor suppressor protein associated with Tuberous Sclerosis Complex).

Metformin also directly enhances autophagy (via phosphorylation of the Raptor-ULK1 complex) as does rapamycin (via phosphorylation of ATG13 and ULK½). By activating AMPK, use of metformin leads to mTORC1 downregulation, IGF-1/AKT pathway downregulation, and p53-mediated cell cycle arrest. These suppressive effects may allow for arrest of tumor progression or may induce cell death. Metformin also suppresses AKT activation, suppresses ERK ½ signaling, reduces expression of tyrosine kinases (EGFR and HER2), and decreases p-MAPK.

Without being bound to a specific theory, resistance to rapamycin in malignancies (and other malignant conditions) may result from AKT activation due to IRS-1 negative feedback on AKT. Metformin inhibits AKT activation by activating AMPK which in turn phosphorylates and, thus, activates IRS-1 at Ser 789. Combining these two agents (metformin and rapamycin) into a simple formulation (especially at lower than standard doses of either drug alone) may overcome resistance to rapamycin without aggravating clinical safety or incurring dose-limiting toxicity.

Multi-drug chemotherapy regimens (such as doxorubicin, paclitaxel, and carboplatin) are associated with serious safety issues and toxicity-precluding widespread use for all but the gravest of malignant conditions. The lower than standard dose combination could augment chemotherapy (for either treatment or prevention) or could be used as a preferred alternative to standard therapies in appropriately selected patients. The drug combination of the present invention may provide a substantially improved safety profile, allowing for better adherence, compliance, tolerability, and persistence on drug while achieving comparable efficacy in well-selected patients with appropriate tumor types and subtypes.

The concept of adding oral standard doses of metformin (500 mg twice daily) to standard dose (25 mg once weekly) intravenous (parenteral) temsirolimus has been tested in a phase I study (involving a variety of malignancies) (Mackenzie M J et al. A phase I study of temsirolimus and metformin in advanced solid tumors. Invest New Drugs 2012; 30:647-652.) and shown to produce serious and dose-limiting toxicity in all patients enrolled in the study (N=11), precluding further drug usage at these doses in these patients. The drug combination of the present invention could substantially improve the safety profile and allow for greater tolerability using relatively low doses of rapamycin with either standard or low doses of metformin (both given orally, locally, topically, or targeted to a specific tissue as a single formulation) for a variety of diseases that include, but are not limited to, both benign and malignant neoplasms.

Everolimus (a rapamycin derivative) was administered together with an oral MEK inhibitor trametinib (GSK1120212) and evaluated in a Phase 1B study in patients with advanced solid tumors (Tolcher A W et al. Annals of Oncology 2015; 26: 58-64). This trial was based on previous in vitro studies demonstrating that concomitant use of trametinib and "rapamycin, an mTOR inhibitor, triggered marked cytotoxicity and synergistic effects". Concurrent treatment with trametinib and everolimus resulted in frequent treatment-related adverse events, including mucosal inflammation (40%), stomatitis (25%), fatigue (54%), and diarrhea (42%)-side effects frequently seen with everolimus but infrequently reported with trametinib. Tolerable combinations of both drugs at doses adequate to achieve efficacy could not be achieved. Because of these substantial safety issues, the investigators stated that "based on the current data, further investigation of everolimus in combination with trametinib is not warranted in patients with solid tumors". Therefore, combining a rapalog with another drug (especially one that affects signal transduction) neither assures safety nor efficacy and is often undesirable.

Cancer stem cells (CSCs) are believed to be a unique and critical subpopulation (≤3.5%) of tumor cells capable of self-renewal activity, tumor initiation, and tumor propagation. CSCs are prone to metastasis. Eradicating CSCs is therefore critical to treating (and controlling) cancer. CSCs are resistant to both radiation therapy and chemotherapy and they proliferate despite high doses of such therapies. CSCs are also associated with high mTORC1 activation states and may be targets of this proposed drug combination.

Tamoxifen is the most widely used hormonal agent for estrogen receptor positive (ER+) breast cancer. Although ER+ breast cancer cells are sensitive to the therapeutic effects of tamoxifen, breast cancer stem cells, a critically important subpopulation, are resistant to tamoxifen and demonstrates enhanced activation of the mTORC pathway (and its downstream targets) when treated with tamoxifen (putting into question the ultimate value of tamoxifen hormonal therapy for chemoprevention). mTORC1 activation is associated with many malignancies and their respective CSCs, including lung, breast, prostate, colon, and liver. Use of a drug combination comprising low or very low (non-standard) doses of metformin and low or very low (non-standard) doses of rapamycin could be a superior therapy for both primary and secondary chemoprevention in patients at risk for incident and recurrent malignancies. Contrary to standard dose therapy with rapamycin, the present drug combination at lower than standard doses allows for an optimized safety profile and addresses both the CSC population of resistant cells as well as the non-CSC population. Such a lower than standard dose combination is consistent with a rationally designed, safer therapeutic indicated for long-term chronic use. Such a combination could be in addition to other chemopreventative therapies, including hormonal therapies (including ER blockade (e.g., tamoxifen) and aromatase inhibitors (e.g., exemestane) and growth factor receptor antagonists. Such a combination could also be considered for use in breast cancer patients who are triple negative (i.e., negative for estrogen receptors, progesterone receptors, and HER2 receptors).

In one embodiment, the drug combination comprises rapamycin and methotrexate. Methotrexate is a known drug and is commonly used to treat various cancers, rheumatoid arthritis, psoriasis, and other indications. The chemical name for methotrexate is N-[4-[[(2,4-diamino-6-pteridinyl) methyl]methylamino]benzoyl]L-glutamic acid. The structural formula is:

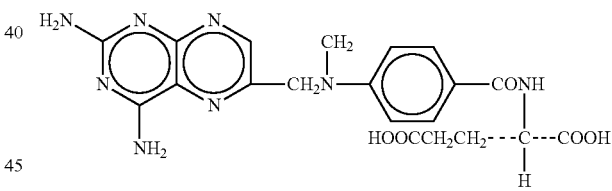

Use of a drug combination comprising rapamycin and methotrexate may reduce the amount of both rapamycin and methotrexate needed for successful treatment when compared to use of either drug by itself. Without being bound by a particular theory, the longer the combination of rapamycin and methotrexate is used, the lower the level of rapamycin needed in the blood to allow for rapamycin activity (e.g., mTOR inhibition). Methotrexate gets polyglutamated within the cell. Up to seven glutamic acid residues can attach to methotrexate. Higher degrees of polyglutamation appear to correlate with enhanced efficacy and are independent of serum levels of methotrexate. Thus, even when serum levels of methotrexate are relatively low, the efficacy of the methotrexate remains. Typically efficacy of rapamycin is correlated with blood levels between 5 and 15 ng/mL. Methotrexate polyglutamates get trapped within the cell and remain active despite low serum levels of methotrexate (and low blood levels of rapamycin). Intracellular polyglutamation of the methotrexate may, thus, improve the efficacy of rapamycin, even when it is given at lower than standard doses.

This pharmacological effect of methotrexate will potentially allow for lower doses of rapamycin to be given with greater degrees of efficacy if the combination is used chronically over weeks to months. This should lead to a sustained pharmacodynamic effect due to the maintenance of long term efficacy in spite of lower dosing of rapamycin which in turn may result in a safer and more convenient regimen with higher degrees of overall efficacy.

The present drug combination could also be used together with the newly developed classes of cancer immunotherapy agents (e.g., checkpoint inhibitors) either alone or concomitant with other chemotherapy agents for a variety of malignancies.

The present drug combination could also be added onto or combined with other anti-inflammatory agents, such as NSAIDs and PDE4 inhibitors (e.g., apremilast).

Rapamycin is an inhibitor of the mTOR pathway. The mTOR pathway has been implicated in a number of diseases and conditions including heritable and inborn genetic conditions; certain malignancies; autoimmune diseases; neurodegenerative diseases; and VEGF-mediated diseases. These diseases and conditions may be better treated or prevented using a combination drug that includes both rapamycin and an AMPK activator.

Heritable and inborn genetic diseases that may be associated with the mTOR pathway include: autism spectrum disorders; autoimmune lymphoproliferative syndrome; autosomal dominant polycystic kidney disease; Bannayan-Riley-Ruvalcaba syndrome (BRRS); Birt-Hogg-Dube Syndrome; blue rubber bleb nevus syndrome; COPA syndrome (mutations in the coatomer subunit alpha (COPA) gene); Cowden disease; epilepsy (Seizure Disorders); cutaneous angiofibromatosis; Duchenne muscular dystrophy and other types of muscular dystrophies, myotonic dystrophy, heart failure due to any etiology, diatolic dysfunction, cardiomyopathy, laminopathies, diseases due to mutations in the LMNA gene responsible for A-type lamins, dystrophies of skeletal muscle and fat, Familial Adenomatous Polyposis (FAP); Primary and Secondary Chemoprevention of malignancy in FAP; Familial mucocutaneous venous malformations; prevention and treatment of dyskeratosis congenita and its associated malignancies (e.g., oropharyngeal carcinoma); prevention and treatment of Fanconi's Anemia and its associated malignancies (e.g., oropharyngeal cancers, myelodysplastic syndrome, and Acute Myeloid Leukemia); prevention and treatment of dyskeratosis; Focal Cortical Dysplasia Type IIB; Gardner's Syndrome; Turcott's Syndrome; Hutchinson-Gilford progeria syndrome; Werner syndrome; Familial multiple discoid fibromas; Sporadic Angiofibromas; Hypertrophic cardiomyopathy; inborn genetic syndromes associated with vascular malformations and hemangiomas (including those associated with TIE2 mutations); LEOPARD syndrome (autosomal dominant PTPN11 mutations); Lhermitte-Duclos disease; lymphangiolciomyomatosis (LAM); Lynch Syndrome; lymphatico-vascular malformations; and other complicated vascular anomalies; Multiple Endocrine Neoplasia Types I and II; Neurofibromatosis type I; Neurofibromatosis type II (associated with neural tumors, e.g., schwannomas); Pachyonychia (congenital); Peutz-Jeghers syndrome; Progeria; progeria-like syndromes; Proteus Syndrome; Proteus-like Syndrome; Juvenile polyposis; PTEN Hamartoma-Tumor Syndromes (PHTS); PMSE (polyhydramnios, megalencephaly, and symptomatic epilepsy) syndrome; Sturge-Weber Syndrome; Seizures associated with Sturge-Weber Syndrome; TIE2-mutated venous malformations; Tuberous Sclerosis Complex (TSC); Cutaneous angiofibromas associated with TSC; Hypopigmented Lesions associated with TSC; lymphangiolciomyomatosis associated with TSC; Renal Angiomyolipoma associated with Tuberous Sclerosis Complex; Seizures associated with TSC; Subependymal Giant Cell Astrocytoma (SEGA) Lesions associated with TSC; spontaneous venous malformations. A combination drug that includes rapamycin (or a rapalog) and an AMPK activator may be used to treat or prevent these conditions, or to treat or prevent the symptoms of these conditions.

Certain malignancies may also be associated the with mTOR pathway including early and Advanced Breast Cancer; bladder cancer and uroepithelial cancers; early and Advanced Renal cell carcinoma; early and Advanced Pancreatic cancers and pancreatic neuroendocrine tumors; pancreatic tumors; B cell malignancies and lymphomas; intraocular lymphoma; Childhood astrocytoma; cholangio-carcinomas; colon cancer (including inborn and heritable conditions that increase the risk for colon cancer); colorectal cancer; colon cancer associated with inflammatory bowel disease; cancer involving any area of the gastrointestinal tract; oropharyngeal cancer; esophageal cancer; Barrett's Esophagus; dermatofibromas; desmoid tumors; desmoid-type tumors; endometrial cancer; epidermal (skin) cancer; Erdheim-Chester disease (a rare form of non-Langerhans' cell histiocytosis), facial angiofibromas; angiofibromas; Gliomas; Glioblastoma; Head and Neck Cancer; Hemangiomas; Hepatocellular carcinomas; Histiocytosis X; Langherhans Cell Histiocytosis; Letterer-Siwe Disease; Hypereosinophilic Syndromes; Leukemias (including acute and chronic leukemias); Lymphoma (of any type); pre-lymphoma conditions (e.g., those associated with Sjogren's Syndrome); lung cancer (of any histological type); Lymphangioleiomyomatosis (LAM); mantle cell lymphoma; cutaneous T cell lymphoma; Sezary Syndrome and Mycoses fungoides; Parapsoriasis, lichen planus; melanoma; non-melanoma skin cancer (including basal cell carcinomas); myeloid neoplasms; Nasopharyngeal Carcinoma; Oropharyngeal Cancer; Osteosarcoma; Port Wine Stains; prostate cancer; Spider Veins; Cherry Angiomas; plasma cell dyscrasias including MGUS (monoclonal gammopathy of undetermined significance), Smoldering Multiple Myeloma, Multiple Myeloma, and Waldenstrom's Macroglobulinemia; Renal Angiomylipoma; renal cell carcinomas and malignancies of any histological type; sarcomas; and Midline Granuloma. A combination drug that includes rapamycin (or a rapalog) and an AMPK activator may be used to treat or prevent these conditions, or to treat or prevent the symptoms of these conditions. Chemoprevention of these conditions (including both benign and malignant neoplasms of any pathological or histological type) can include either primary or secondary chemoprevention or both. Primary prevention may be used to prevent a condition from occurring and treatment may begin before a diagnosis is made. Secondary prevention may be used in patients who have or had a condition, in which the condition was treated resulting in remission, a cure, or the condition being considered "under control." Secondary prevention may be used to prevent the development of a second primary or second new event or recurrence.

Autoimmune diseases and syndromes may also be associated with the mTOR pathway and include immunologically mediated conditions, inflammatory conditions and autophagy related disorders. These conditions may include: Antiphospholipid antibody syndrome; Autoimmune cytopenias; Autoimmune hemolytic anemia; Autoimmune hepatitis; Autoimmune lymphoproliferative syndrome; Atopic dermatitis; Ankylosing spondylitis and Axial spondyloarthropathies; acne vulgaris, Bronchial asthma; Bronchial Asthma with Eosinophila; Crohns disease; Ulcerative Colitis; Inflammatory Bowel Disease; Celiac Disease; Dermatomyositis; polymyositis; dermatomyositis/polymyositis syndromes associated with any particular autoantibody; CREST Syndrome; Type 1 Diabetes Mellitus; Discoid lupus; lupus panniculitis; bullous lupus erythematosus; subacute cutaneous lupus erythematosus; systemic lupus erythematosus (SLE); cutaneous lupus crythematosus; lupus nephritis; cytopenias associated with SLE; central nervous system SLE (CNS Lupus); Eosinophilic esophagitis; Eosinophilic Granulomatosis with Polyangiitis (EGPA; Churg Straus Syndrome); Evan's syndrome; Graft vs. Host Disease; Humoral/Cellular immunodeficiency disorders; hidradenitis supporativa; hypopigmentation disorders involving the skin, Immune thrombocytopenia purpura (Autoimmune Thrombocytopenia Purpura; Idiopathic Thrombocytopenia Purpura); Juvenile idiopathic Arthritis of any type; keloids and scars; non-alcoholic steatohepatitis (NASH); Osteoarthritis; Osteoarthritis Associated With Diabetes Mellitus and Insulin Resistant States; Psoriasis; Psoriatic Arthritis; Renal Transplantation; Rheumatoid arthritis; SLE (systemic lupus erythematosis); Bullous pemphigus; Pemphigus vulgaris; Bullous pemphigoid; Neuromyelitis optica (NMO); Myasthenia gravis; Multiple sclerosis; Guillain Barre syndrome; CIDP (chronic inflammatory demyelinating polyneuropathy); Optic neuritis; Sarcoidosis; unstable angina pectoris and unstable plaque with atherosclerosis and coronary heart disease; aortic aneurysm; Uveitis of multiple etiologies; primary and secondary Sjogrens Syndrome; Primary Biliary Cholangitis (Primary Biliary Cirrhosis); Isolated CNS vasculitis; Autoimmune Hepatitis; Peripheral Demyelinating Polyneuropathy; Behcet's syndrome; Takayasu's arteritis; Giant cell arteritis/temporal arteritis; Mixed cryoglobulinemia; Polymyalgia rhematica; Idiopathic inflammatory myopathies/myositis; Granulomatosis and polyangiitis (Wegener's granulomatosis); Microscopic polyangiitis (MPA); ACPA positive vasculitis; Cogan's syndrome; Autoimmune sensorineural hearing loss; vitiligo; melasma; joint disease characterized by inflammation; and chronic pain associated with inflammatory diseases including inflammatory arthritis. A combination drug that includes rapamycin (or a rapalog) and an AMPK activator may be used to treat or prevent these conditions, or to treat or prevent the symptoms of these conditions. The drug combination may also be used as a steroid sparing agent for any of the above disorders. The drug combination may also be used to treat post-operative pain caused by inflammation.

In one embodiment of the invention, the drug combination may be used to treat a joint disease characterized by inflammation. Such diseases include inflammatory arthritis of any etiology and are characterized by inflammation of the synovial membrane. Topical application of the drug combination of rapamycin and metformin may be directly over or on top of an inflamed or diseased joint to provide the most effective treatment.

The mTOR pathway has also been implication in neurodegenerative diseases, protein deposition diseases; and autophagy related diseases. These diseases and disease conditions include Alzheimer's disease; Beta amyloidopathies; dementia; Head-trauma related dementia; Huntingdon disease; Tauopathies; Parkinson's disease; Presenile dementia; Amyloid Associated Vasculopathies; Frontotemporal Dementia; Lewy Body Dementia; Amyotrophic Lateral Sclerosis (ALS); and refractory seizures. A combination drug that includes rapamycin (or a rapalog) and an AMPK activator may be used to treat or prevent these conditions, or to treat or prevent the symptoms of these conditions. The drug combination may also be used for neuroprotection, including neuroprotection post-stroke and after head trauma.

Other diseases or conditions associated with the mTOR pathway include vascular endothelial growth factor (VEGF) mediated diseases or diseases associated with VEGF and HIF-1 alpha. VEGF is a signal protein produced by cells that stimulates vasculogenesis and angiogenesis. HIF-1 alpha stimulates VEGF and is associated with high VEGF states. mTOR activation leads to high levels of HIF-1 alpha production. Laser treatment of cutaneous vascular lesions results in activation of mTOR and overproduction of VEGF. Overproduction of VEGF can contribute to disease and disease conditions including Age-related macular degeneration; Angiofibromas; blue rubber bleb nevus syndrome; capillary venous malformations; complex vascular neoplasms; disseminated neonatal hemangiomata; cavernous hemangiomas; Fibrotic conditions; Epithelioid hemangioendothelioma; Diabetic retinopathy; Diabetic nephropathy; diffuse telangiectatic facial erythema; erythrotelangiectatic rosacea; diffuse microcystic lymphatic malformations; fibromas; spider veins; hemangioendotheliomas; Klippel-Trenauncy syndrome; hemangioendothelioma; Maffucci Syndrome associated with hemangioendothelioma; Infantile hemagioma; PHACE syndrome associated with infantile hemangioma; cutaneous vascular lesions that tend to recur after treatment with lasers (i.e.; use our combination product to prevent recurrence of these vascular lesions (e.g., port wine stains) following use of lasers, especially pulsed dye lasers); Complications from Intra-arterial stents (for use in stents to prevent thrombosis); Kaposi's sarcoma (KS) (both skin and systemic manifestations) (KS associated with organ transplantation, HIV, or seen in elderly people); kaposiform hemangioendothelioma; port wine stains; port wine stains associated with Sturge-Weber Syndrome; spider veins; cherry angiomata; skin transplantation; telangiectases; vascular malformations occurring de novo or associated with an inborn genetic mutation (e.g., TIE2 mutation; rosacea. A combination drug that includes rapamycin (or a rapalog) and an AMPK activator may be used to treat or prevent these conditions, or to treat or prevent the symptoms of these conditions. The drug combination may also be used as a VEGF sparing agent for any of the above disorders.

Inhibition of the mTOR pathway also has been associated with increased longevity and delaying of aging in laboratory animals. The use of an AMPK activator such as metformin or methotrexate in combination with rapamycin may allow for a lower dose of rapamycin to be used as an effective prophylactic antiaging therapy. Such prophylaxis could result in either extension of life or a healthier aging process with fewer associated co-morbidities such diabetes, cardiovascular disease, heart failure and diastolic dysfunction, and dementia. Such a drug combination, especially when administered topically, could be used for skin rejuvenation and treatment/prevention of wrinkling and reduction of the effects of sun damage and UV light exposure.

In an aspect of the invention, the combination drug may be used to treat any condition associated with the mTOR pathway, including heritable and inborn genetic diseases, malignancies, renal transplantation, autoimmune and immunologically mediated inflammatory diseases, neurodegenerative diseases, and VEGF mediated diseases.

In one embodiment, the combination drug may be used to treat tuberous sclerosis complex (TSC). TSC is a rare condition that affects 25,000-40,000 patients in the United States and up to 2 million patients globally. It occurs in 1:6000 births and is caused by a genetic mutation in either of 2 oncogene suppressors leading to excessive mTOR complex 1 (mTORC1) activity. Symptoms of the condition vary but can include systemic hamartomas (large and small tumorous growths) on the brain, eye, skin, heart, lungs, and kidneys and intractable seizures from CNS lesions leading to cognitive decline. There is currently no approved therapeutic agent for modifying the course of the disease including seizures, cognitive decline, and behavioral disorders. Cutaneous TSC disease is a progressive disease that results in a visible manifestation of the multi-organ disease and can result in significant and disfiguring skin conditions.

In another embodiment, the combination drug may be used to treat polyhydramnios, megaencephaly, and symptomatic epilepsy (PMSE) syndrome. PMSE syndrome is an ultra-rare neurodevelopmental disorder found among the Old Order Mennonite population. It is caused by a homozygous deletion of exons 9 to 13 of the LYK5/STRADA gene responsible for encoding a protein called STRADα (pseudokinase STE20-related kinase adaptor α), an upstream inhibitor of mTORC1. PMSE syndrome is characterized by infantile-onset, treatment-resistant multifocal epilepsy, severe cognitive delays, and craniofacial dysmorphism. Patients with PMSE syndrome face an increased risk of death from epilepsy and 38% of PMSE patients die before age 6. There are currently no approved therapeutic agents for altering the course of the condition.

In one embodiment, the combination drug may be used to treat early stage Alzheimer's Disease (AD). Rapamycin has been shown to induce autophagy through mTOR inhibition and significantly reduce plaques, tangles, and cognitive defects in mice when given before the establishment of plaques and tangles in the brain. Majumder, et al., PLOS ONE, 2011; 9(6): e25416. Thus, the combination drug may be more effective at preventing the development of beta-amyloid plaques when used early in the disease process.

In one embodiment, the combination drug may be used to treat Kaposi's sarcoma (KS). KS is a human herpesvirus 8 associated malignancy associated with immunosuppression. It is most commonly seen in patients with HIV/AIDS, and transplant patients. There are geographic and ethnic predispositions to KS.

In one embodiment, the inflammatory skin disease may be atopic dermatitis (eczema).

In one embodiment, the combination drug may be used to treat two related autoimmune diseases: skin disease associated with systemic lupus erythematosus (SLE) and discoid lupus erythematosus (DLE). These conditions are autoimmune inflammatory diseases that affect the skin and produce persistent scaly, disk-like plaques on the scalp, face, and ears and may cause pigmentary changes, scarring, and hair loss.

In one embodiment, the combination drug may be used to treat pachyonychia congenita, an ultra-rare autosomal dominant disease that affects several thousand people worldwide. The disease is caused by a mutation in one of five keratin genes: K6a, K6b, K6c, K16, or K17. The disease causes focal palmoplantar hyperkeratosis, hypertrophic nail dystrophy, follicular hyperkeratosis, and oral leukokeratosis. It does not affect lifespan. Trials have been conducted to assess whether rapamycin might be effective in treating pachyonychia congenita. The systemic side effects of oral rapamycin limited the trials. Use of the combination drug would reduce these systemic side effects by reducing the amount of rapamycin in each dose, by reducing the frequency of dosing, or both.

In one embodiment, the combination drug may be used to treat a PTEN Hamartoma Tumor Syndrome, which includes Cowden Syndrome (CS) Lhemitte-Duclos disease (LD), Bannayan-Riley-Ruvalcaba syndrome (BRRS), osteoarthritis, and Proteus Syndrome (PS).

Any route of administration of the combination drug may be effective in treating TSC. For example an oral or parenteral (subcutaneous, intramuscular, or intravenous) route of administration may be effective in treating the progression of the disease and to control or prevent symptoms such as seizures and cognitive decline. A topical treatment may be used to treat cutaneous TSC. Proper formulation and dosages will depend on the specifics of the patient (age, weight, etc.).

Proper formulation and dosages will depend on the disease condition to be treated. The drug combination may be administered in any manner that is suitable for treating the desired condition.

Any suitable dosage formulation for administering the combination may be used for treatment. For example, the combination may be incorporated into a tablet, capsule, or a liquid formulation for oral administration; a cream, lotion, ointment, gel, or paste for topical administration; or in a liquid, lyophilized form, or nanoparticle form for parenteral administration; or a viscous base for intraarticular administration (e.g., together with hyaluronic acid).

The above dosage forms will also include the necessary carrier material(s), excipient(s), lubricant(s), buffer(s), or the like.

The drug combination of the present invention may be used in pharmaceutical compositions. These pharmaceutical compositions can be used in the preparation of individual, single unit dosage forms. Pharmaceutical compositions and dosage forms can comprise the drug combination as described herein or a pharmaceutically acceptable salt or solvate thereof. Pharmaceutical compositions and dosage forms can further comprise one or more carriers, excipients or diluents.

Non-limiting examples of possible dosage forms include tablets; caplets; capsules, such as soft elastic gelatin capsules; cachets; troches; lozenges; dispersions; suppositories; powders; aerosols (e.g., nasal sprays or inhalers); topical dosage forms such as gels; creams, lotions, and ointments; liquid dosage forms suitable for oral or mucosal administration to a patient, including suspensions (e.g., aqueous or non-aqueous liquid suspensions, oil-in-water emulsions or a water-in-oil liquid emulsions), solutions and elixirs.

The pharmaceutical compositions comprising the drug combinations may be suitable for oral administration and can be presented as discrete dosage forms, such as, but not limited to, tablets (e.g., chewable tablets), caplets, capsules and liquids (e.g., flavored syrups). Such dosage forms contain predetermined amounts of active ingredients as described herein and can be prepared by methods of pharmacy well known to those skilled in the art.

Such dosage forms can be prepared by any of the methods of pharmacy. In general, pharmaceutical compositions and dosage forms for oral administration are prepared by uniformly and admixing the active ingredients with liquid carriers, finely divided solid carriers or both and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Typical oral dosage forms are prepared by combining the active ingredients in an admixture with at least one excipient according to conventional pharmaceutical compounding techniques. Excipients can take a wide variety of forms depending on the form of preparation desired for administration. Non-limiting examples of excipients suitable for use in oral liquid or aerosol dosage forms include water, glycols, oils, alcohols, flavoring agents, preservatives and coloring agents. Non-limiting examples of excipients suitable for use in solid oral dosage forms (e.g., powders, tablets, capsules and caplets) include starches, sugars, micro-crystalline cellulose, diluents, granulating agents, lubricants, binders and disintegrating agents.

Non-limiting examples of excipients that can be used in oral dosage forms include binders, fillers, disintegrants and lubricants. Non-limiting examples of binders suitable for use in pharmaceutical compositions and dosage forms include corn starch, potato starch or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose and mixtures thereof.

Non-limiting examples of suitable forms of microcrystalline cellulose include, but are not limited to, the materials sold as AVICEL® (microcrystalline cellulose) PH-101, AVICEL® (microcrystalline cellulose) PH-103, AVICEL RC-581® (crystalline cellulose and carboxymethylcellulose sodium), AVICEL® (microcrystalline cellulose) PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581® (crystalline cellulose and carboxymethylcellulose sodium). Suitable anhydrous or low moisture excipients or additives include AVICEL-PH-103™® (microcrystalline cellulose) PH-103 and Starch 1500® LM (pregelatinized starch).

Non-limiting examples of fillers suitable for use in the pharmaceutical compositions and dosage forms disclosed herein include talc, calcium carbonate (e.g., granules or powder), microcrystalline cellulose, powdered cellulose, dextrates, kaolin, mannitol, silicic acid, sorbitol, starch, pregelatinized starch and mixtures thereof. The binder or filler in pharmaceutical compositions is typically present in from about 50 to about 99 wt. % of the pharmaceutical composition or dosage form.

Disintegrants are used in the compositions to provide tablets that disintegrate when exposed to an aqueous environment. The amount of disintegrant used varies based upon the type of formulation and is readily discernible to those of ordinary skill in the art. Typical pharmaceutical compositions comprise from about 0.5 to about 15 wt. % of disintegrant, from about 1 to about 10 wt. %, or from about 1 to about 5 wt. % of disintegrant.

Non-limiting examples of disintegrants that can be used in pharmaceutical compositions and dosage forms include agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums and mixtures thereof.

Non-limiting examples of lubricants that can be used in pharmaceutical compositions and dosage forms include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laureate, agar and mixtures thereof. When present, lubricants may be used in an amount of less than about 1 wt. % of the pharmaceutical compositions or dosage forms.

The dose administered must be carefully adjusted according to age, weight and condition of the patient, as well as the route of administration, dosage form and regimen and the desired result.

In one embodiment, the drug combination may be formulated for oral administration or sublingual administration. In one embodiment, the drug combination may comprise rapamycin and methotrexate in a ratio of approximately 1:2, approximately 1:2.5, approximately 1:3, approximately 1:3.5, or approximately 1:4. In one embodiment, rapamycin may be present in an amount of about 0.5 mg, about 1 mg, about 2 mg, about 3 mg, about 4 mg, about 5 mg, about 6 mg, about 7 mg, about 8 mg, or even about 9 mg. Methotrexate may be present in an amount of about 6 mg, about 9 mg, about 12 mg, about 15 mg, about 18 mg, about 21 mg, about 24 mg, or even about 27 mg. Methotrexate may also be given in about 2.5 mg multiples up to about 25 mg (about 2.5 mg, about 5.0 mg, about 7.5 mg, about 10 mg, about 12.5 mg, about 15 mg, about 17.5 mg, about 20 mg, about 22.5 mg, and about 25 mg).

In one embodiment rapamycin may be present in an amount ranging from about 0.5 mg to about 10 mg and methotrexate in the range of from about 3 mg to about 30 mg in the same oral dosage form. In another embodiment rapamycin may be present in an amount ranging from about 0.5 mg to about 8 mg and methotrexate in the range of from about 5 mg to about 25 mg in the same oral dosage form. Here as elsewhere in the specification and claims, ranges can be combined to form new and non-disclosed ranges.

In one embodiment, the rapamycin may be present in an amount of about 0.5 mg, about 1 mg, about 2.0 mg, about 2.5 mg, about 3.0 mg, about 3.5 mg, about 4.0 mg, about 4.5 mg, or about 5.0 mg. Methotrexate may be present in an amount of about 7.5 mg, about 8.0 mg, about 8.5 mg, about 9.0 mg, about 9.5 mg, or about 10.0 mg.

In another embodiment, the drug combination may be used to treat heritable and inborn genetic diseases. A lower or higher dose of methotrexate as compared to rapamycin may be suitable to treat or prevent these diseases. The ratio of the combination of rapamycin and methotrexate may be about 2:1 (rapamycin to methotrexate) or about 1:2; about 1:2.5; about 1:3; about 1:3.5; and about 1:4.

The drug combination may be administered orally up to one tablet per day. Because of the potential side effects of the drugs, especially the methotrexate, it is preferable to administer the drug combination less frequently. In one embodiment, the drug combination is administered in a once weekly dose. In another embodiment, the drug combination is administered weekly but in two half doses, with the second dose being given 24 hours after the first dose.

The drug combination may be administered orally up to one tablet per day. Sublingual administration may achieve a higher blood level of the drug combination with a lower dose of drug due to enhanced absorption. Thus, it may be preferred to administer the sublingual formulation once weekly.

Use of an additive or synergistic agent (e.g., an AMPK activator such as methotrexate)) with rapamycin may enhance efficacy, lower the required dose of the rapamycin and/or decrease the frequency of drug administration. In one embodiment, the drug combination may be administered in a once weekly pulsed regimen. This dosing regimen may alleviate potential side effects seen with use of rapamycin, methotrexate, or both including undesired immunosuppression, stomatitis, hyperlipidemia, hyperglycemia, and cytopenia.

In one embodiment, the drug combination may be formulated as a rectal suppository, especially for treatment of infants and children. The same general dosing regimen as for oral administration would apply to a rectal suppository formulation.

In one embodiment, the drug combination may be formulated for intra-articular administration. This formulation may be used to treat joint diseases characterized by inflammation. In one embodiment, the joint disease is osteoarthritis (e.g., osteoarthritis of the knee joint) or inflammatory arthritis involving a specific joint. The drug combination may include viscosupplementation as a base (e.g., hyaluronic acid). The hyaluronic acid may serve as the medium into which the drug combination is added. In one embodiment, the drug combination of rapamycin and methotrexate is added to a medium comprising hyaluronic acid. The rapamycin may be added in an amount of about 0.5 mg, about 1.0 mg, about 1.5 mg, about 2.0 mg, about 2.5 mg, even about 5.0 mg. The methotrexate maybe a added in an amount of about 4.0 mg, about 4.5 mg, about 5.0 mg, about 5.5 mg, about 6.0 mg, even about 8.0 mg. This formulation may be administered via intra-articular administration into a joint (e.g., a knee joint) every 2-3 months up to 3 times per year. In another embodiment, the drug combination may include rapamycin and metformin or any other AMPK activator. In another embodiment, the drug combination may contain rapamycin, methotrexate, and another AMPK activator.

Tablets of various sizes can be prepared, e.g., of about 2 mg to 2000 mg in total weight, containing both of the active substances in the ranges described above, with the remainder being a physiologically acceptable carrier of other materials according to accepted pharmaceutical practice. These tablets can, of course, be scored to provide for fractional doses. Gelatin capsules can be similarly formulated. Unique color coatings and markings may be used for easy identification for patients to enhance safety and compliance and create branding.

In one embodiment, the drug combination may be in a liquid formulation. Liquid formulations may be prepared by dissolving or suspending the combination of active substances in a conventional liquid vehicle acceptable for pharmaceutical administration so as to provide the desired dosage in one to two teaspoonfuls. Such dosage forms can be administered to the patient on a regimen of one to two doses per day. Special coloring and flavoring may be added to enhance compliance and create branding.

In one embodiment, the drug combination may be formulated for parenteral administration. As with the oral formulation, the drug combination may comprise rapamycin and methotrexate in a ratio of approximately 1:2, approximately 1:2.5, approximately: 3, approximately 1:3.5, or approximately 1:4 and approximately 1:4.5. In one embodiment, rapamycin may be present in an amount of about 3 mg, about 4 mg, about 5 mg, about 6 mg, about 7 mg, about 8 mg, or even about 9 mg. Methotrexate may be present in an amount of about 9 mg, about 12 mg, about 15 mg, about 18 mg, about 21 mg, about 24 mg, or even about 27 mg or about 7.5 mg, about 10 mg, about 12.5 mg, about 15 mg, about 17.5 mg, about 20 mg, about 22.5 mg, about 25 mg, and about 27.5 mg.

In one embodiment, rapamycin may be present in an amount ranging from about 0.5 mg to about 10 mg and methotrexate in the range of from about 2.5 mg to about 30 mg in the same oral dosage form. In another embodiment, rapamycin may be present in an amount ranging from about 0.5 mg to about 8 mg and methotrexate in the range of from about 5 mg to about 25 mg in the same oral dosage form.

In one embodiment, the rapamycin may be present in an amount of about 0.5 mg, about 1 mg, about 1.5 mg, about 2 mg, about 2.5 mg, about 3.0 mg, about 3.5 mg, about 4.0 mg, about 4.5 mg, or about 5.0 mg. Methotrexate may be present in an amount of about 5.0 mg, about 7.5 mg, about 8.0 mg, about 9.0 mg, or about 10.0 mg.

In another embodiment, the drug combination may be used to treat heritable or inborn genetic diseases. A lower or higher dose of methotrexate as compared to rapamycin may be suitable to treat or prevent these diseases. The ratio of the combination of rapamycin and methotrexate may be about 2:1 (rapamycin to methotrexate) or about 1:2, or about 1:3, or about 1:4, or about 1:5.

In one embodiment, the parenteral (subcutaneous) formulation of the drug combination may be administered once weekly by injection, including by autoinjection. In another embodiment, the parenteral formulation may be administered weekly in two half doses, with the second half dose being administered 24 hours after administration of the first half dose.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the excipients which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Sustained release forms of such formulations may be used and may provide such amounts biweekly, weekly, monthly, etc. A dosing period of at least one to two weeks is required to achieve minimal benefit.

In one embodiment, the drug combination may be formulated for topical (cutaneous), localized, tissue-targeted, or site-specific administration. Such formulations may be in the form an ointment, cream, lotion, gel, or paste. Topical formulations also include eye drops and nasal sprays. Such dosages may include rapamycin in the amount of about 0.01%, about 0.025%, about 0.05%, about 0.75%, about 0.1%, about 0.25%, about 0.5%, about 0.75%, about 1.0%, about 1.5%, about 2.0%, about 2.5%, about 3.0%, about 3.5%, or about 4.0% by weight of rapamycin. In one embodiment, the amount of rapamycin is in the range of about 0.01% to about 4.0% by weight; about 0.1% to about 3.5% by weight; about 0.25 to about 3.0% by weight; about 0.5% to about 2.5% by weight; about 0.75% to about 2.0% by weight; about 1.0% to about 2.5% by weight. Metformin (or methotrexate) may be present in this dosage in an amount of about 0.1%, about 0.2%, about 0.5%, about 1.0%, about 1.5%, about 2.0%, or about 2.5% by weight of metformin (or methotrexate).

In one embodiment, a formulation of the drug combination may include a molar ratio of rapamycin to metformin in the range of about 20:1 to about 1:1; about 20:1 to about 3:1; about 20:1 to about 4:1; about 20:1 to about 5:1; about 15:1 to about 1:1, about 15:1 to about 3:1; about 15:1 to about 4:1; about 15:1 to about 5:1; about 10:1 to about 3:1; about 10:1 to about 4:1; about 10:1 to about 5:1; about 5:1 to about 4:1; about 5:1 to about 3:1; or about 5:1 to about 1:1. In one embodiment, the formulation is a topical formulation.

In one embodiment, a formulation of the drug combination may include rapamycin in an amount of up to 4.0 grams. In another embodiment, the formulation may include rapamycin in a range of about 0.01 to about 4.0 grams; about 0.1 grams to about 3.5 grams; about 0.25 to about 3.0 grams; about 0.5 to about 2.5 grams; about 0.7 to about 2.0 grams; or about 1.0 to about 2.5 grams. In one embodiment, the formulation of the drug also may include metformin in an amount of up to 0.7 grams. In another embodiment, the formulation of the drug also may include metformin in a range of about 0.7 grams to about 0.00007 grams, about 0.7 grams to about 0.0007 grams, about 0.7 grams to about 0.007 grams, about 0.7 grams to about 0.45 grams, about 0.7 grams to about 0.028 grams, about 0.6 grams to about 0.02 grams, or about 0.6 grams to about 0.01 grams. In one embodiment, the formulation is a topical formulation.

In one embodiment, the topical formulation is a gel comprising rapamycin and an activator of AMP kinase such as methotrexate or metformin. In one embodiment, the gel comprises a combination of rapamycin and metformin as the active ingredient and at least one excipient.

In one embodiment, the molar ratio of rapamycin to metformin in the gel formulation is in the range of about 20:1 to about 1:1; about 20:1 to about 3:1; about 20:1 to about 4:1; about 20:1 to about 5:1; about 15:1 to about 1:1, about 15:1 to about 3:1; about 15:1 to about 4:1; about 15:1 to about 5:1; about 10:1 to about 3:1; about 10:1 to about 4:1; about 10:1 to about 5:1; about 5:1 to about 4:1; about 5:1 to about 3:1; or about 5:1 to about 1:1. In one embodiment, the gel formulation contains rapamycin in the range of about 0.1 grams to about 4.0 grams and metformin in the range of about 0.00007 grams to about 0.60 grams. In another embodiment, the gel formulation contains rapamycin in the range of about 1.0 grams to about 3.0 grams and metformin in the range of about 0.007 grams to about 0.42 grams.

The gel formulation also includes excipients. Suitable excipients include emulsifiers, organogelators and emollients. Emulsifiers include polyethylene glycol stearate, a glycol stearate, a glyceryl stearate, cetearyl alcohol and ceteareth 20, methylcellulose, Cetomacrogol 1000, and lecithin. Suitable organogelators include 4-tertbutyl-1-aryl cyclohecanols derivatives, polymeric (e.g. poly(ethylene glycol), polycarbonate, polyesters, and poly(alkylene), Gemini gelators (e.g. N-lauroyl-L-lysine ethyl ester), Boc-Ala(1)-Aib(2)-.beta.-Ala(3)-OMe (synthetic tripeptide), and low molecular weight gelators (e.g. fatty acids and n-alkanes). Suitable emollients include cetostearyl alcohol, cetyl alcohol, isopropyl palmitate, caprylic/capric triglyceride, PPG-2 myristyl ether propionate, dimethicone, methicone, petrolatum, lanolin, and mineral oil.

If desired, other additives including surfactants, penetration enhancers, preservatives, viscosity modifiers, and emulsion stabilizers may be included in the mannitol compositions. Suitable surfactants include sodium lauryl sulfate, cetostearyl alcohol, ceteareth 12, ceteareth 20, cetearyl alcohol, Cetomacrogol 1000, stearic acid, and poloxamer. Suitable penetration enhancers include propylene glycol. Suitable preservatives include methylparaben, propylparaben, ethylhexylglycerin, phenoxyethanol, chlorocresol, potassium sorbate, sorbic acid, bronopol, methychloroisothiazolinone, and methylisothiazolinone. Suitable viscosity modifiers include carboxymethylcellulose, carboxyethylcellulose, acrylate crosspolymer, and carbomer. Suitable emulsion stabilizers include xanthan gum, glyceryl stearate, and carbomer.

Other additives may be added such as aromatic agents, antiseptics, and colorants In one embodiment, a topical formulation of the drug combination may include rapamycin and at least two AMPK activators. In one embodiment, a topical formulation of the drug combination includes rapamycin, methotrexate, and about 0.5% to about 27.0% salicylic acid in 0.5% increments by weight of salicylic acid.

In one embodiment, a topical formulation may include topical rapamycin and topical metformin. Rapamycin would be used in a concentration ranging from about 0.1% to about 2.5% and metformin would be used in a concentration ranging from about 0.02% to about 1.5%. These ranges would allow usage of these drugs topically for many different indications.

The drug combination may also be administered through intravitreal, or subconjunctival injection, or topically. For intravitreal or subconjunctival injection, the methotrexate dose would be about 200 mcg per 0.1 mL or about 400 mcg per 0.1 mL. For intravitreal or subconjunctival injection, the rapamycin dose would be about 50 pg per mL to about 200 mcg/mL. Intravitreal injections of the combination could also include rapamycin at a dose of about 350 mcg to about 450 mcg every two months as needed or subconjunctival injections of rapamycin at a dose of about 1300 mcg at days 0, 60 and 120. For topical ophthalmic administration, the dose of rapamycin would be about 50 pg per mL to about 50 mcg per mL and the methotrexate dose would be about 200 mcg per 0.1 mL in a formulation which may be applied at bedtime and throughout the day. The topical formulation may be in a solution, a suspension, an emulsion, and it may be administered in the form of eyedrops, a cream, an ointment, a gel, or an injectable to the eye and/or the eyelid. The combination containing rapamycin may also be administered in milligram quantities as a surgical implant that could be contained in a diffusible walled reservoir embedded and sutured to the wall of the sclera or contained within a carrier system such as liposomes to allow for slow release of the drug combination.

In one embodiment, the drug combination may comprise rapamycin and metformin. This combination may be preferable for patients with diabetes, metabolic syndrome, hyperlipidemia, and/or methotrexate intolerance, as well as for chemoprevention of both malignant and non-malignant neoplastic and non-neoplastic diseases, neurodegenerative diseases such as Alzheimer's disease, and multiple autoimmune and chronic inflammatory disorders. Metformin would be given in a dosage in a range of about 100 mg to about 1000 mg or about 300 mg to about 900 mg. The metformin may be present in amount of about 150 mg, about 300 mg, about 500 mg, about 600 mg, about 700 mg, about 800 mg, about 900 mg, or about 1000 mg. The metformin may be present in an amount of about 166 mg, about 333 mg, about 666 mg, about 1200 mg or about 200 mg, about 400 mg, about 800 mg, or about 1200 mg. Rapamycin would be given in a dosage of about 0.15 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, 1.5 mg, about 2.0 mg, about 2.5 mg, and about 3.0 mg. This formulation could be given orally as a once daily pill. Other dosing regimens may be suitable for different indications.

In one aspect of the invention, a patient in need of treatment may be evaluated with a companion diagnostic to determine whether treatment with a combination drug would be efficacious. The method includes determining a patient's baseline mTOR activation state (including the activation state of mTORC1 downstream pathway components). A finding of a high mTOR activation state would indicate a greater likelihood of success. A finding of normal or low mTOR activity state would indicate a lower likelihood for success. After several weeks of treatment, any change in the patient's mTOR activation state will help determine if the given dose is the correct dose. If mTOR activity has not dropped, an increased dose may be necessary. If drug resistance is suspected, treatment may be stopped. This pharmacodynamics biomarker of response will help guide therapy. Tissue-specific mTOR activation state may be assumed using a biomarker (e.g, an imaging biomarker such as MRI or ultrasound to determine the presence or absence of synovitis), immunohistochemistry (using biopsy tissue), or a localized, salivary, secretory, or peripheral blood biomarker yet to be determined.

The change in mTOR activation state from baseline (e.g., at weeks 2, 4, or 6) may be used to predict future outcome (success) at a later point in time (e.g., at 24-48-52 weeks). This is a predictive biomarker of response.

The phosphorylation status of downstream activation proteins that get phosphorylated by mTORC1 (such as p70S6 ribosomal kinase; S6 protein; 4E-BP1, and cIF4B) and mTOR itself (phospho-mTOR) may be evaluated (by either immunohistochemistry of biopsied tissue or FACS (fluorescent activating cell sorting) analysis of circulating lymphocytes or other formed elements) to determine high mTOR activation states. Rapamycin would inhibit mTORC1 and the phosphorylation of downstream proteins but no change would occur in the total level of these proteins.

mTORC1 inhibition promotes autophagy. Inadequate autophagy is associated with many of the diseases and conditions being targeted by the proposed drug combinations. A companion diagnostic for these drug combinations would determine baseline levels/states of autophagy and the effect on such levels posttreatment. The determination of autophagy level/state using specific biomarkers of autophagy would allow for better patient profiling of who would and would not benefit from the drug combination both at baseline and at early treatment. Prediction of long term response is a potential outcome of such an autophagy biomarker as well as its use to guide adequate dosing.

EXAMPLES $^3$H-Thymidine Uptake Assay
Renal Cell Carcinoma

Pilot plating experiments using Human kidney clear cell carcinoma cell line Caki-I (HTB-46). The cells were exposed to various dosages of rapamycin, methotrexate, and metformin (see Tables below for dosages) to assess inhibition of DNA synthesis/replication. 0.1% DMSO, the test article solvent, in media was the control.

The cells were passaged onto 24-well plates at a concentration of 30,000 cells/well, in total medium volume of 1 mL (RPMI 1640+10% FBS+antibiotics). The cells were then allowed to attach and were incubated from 24 hours before treatment. Cells were then treated, in triplicate, with various concentrations of treatment articles.

$^3$H-thymidine (1 mCi/mL) was diluted to 1 μCi in 5 μL of medium (RPMI 1640+10% FBS+antibiotics) and then added to each well at either 18- or 42-hr post treatment, for the 24- and 48-hr time points respectively.

Cells were then washed three times with 1 ML of DPBS at 24- or 48-hr post treatment to remove unincorporated $^3$H-thymidine. Each well of cells was then lysed in 0.5 mL of 0.5N NaOH+0.5% SDS. Lysate was then transferred to scintillation tubes containing 1 mL if scintillation fluid for counting (3 min/sample).

The results of the pilot plating experiments are summarized below.

TABLE 1

Pilot Plating Experiment-Human kidney clear cell carcinoma cell line Caki-I

| Treatment Article | 24-hr post treatment Average cpm | 48-hr post treatment Average cpm |
|---|---|---|
| Rapamycin 20 nm | 12044 | 6349 |
| Rapamycin 10 nm | 12611 | 7463 |
| Rapamycin 5 nm | 14805 | 8584 |
| Rapamycin 0 nm | 27457 | 12818 |
| Methotrexate 20 nm | 26144 | 11273 |
| Methotrexate 10 nm | 27266 | 20251 |
| Methotrexate 5 nm | 31148 | 16772 |
| Methotrexate 2.5 nm | 30659 | 4811 |
| Methotrexate 0 nm | 27457 | 12818 |
| Metformin 50 nm | 30699 | 11141 |
| Metformin 20 nm | 28060 | 10624 |
| Metformin 10 nm | 34530 | 13671 |
| Metformin 5 nm | 29246 | 12001 |
| Metformin 1 nm | 29394 | 10074 |
| Metformin 0 nm | 65587 | 13295 |

It was noted that the 48-hr incorporation was less than the 24-hr incorporation, suggesting that the cells had been growth arrested or had overgrown the well and sloughed off.

For the next phase of the experiment, the Caki-1 cells were tested with the following treatment articles and evaluated at 24 hours post treatment:

Rapamycin: 10 nM. 5 nM, 1 nM

Methotrexate: 100 nm

Metformin: 5 nm, 1 nm, 0.5 nm

Rapamycin+methotrexate: 5 nm+100 nm, 1 nm+100 nm

Figure 2:
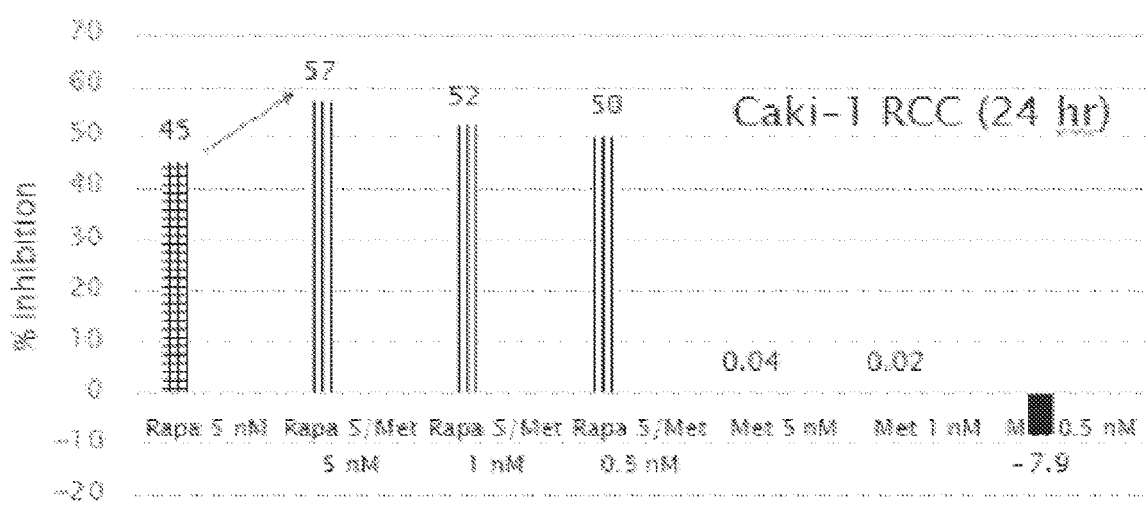
FIG. 2 is a bar graph depicting the percent inhibition of $^3$H-uptake of different doses of rapamycin and metformin alone or in combination in Caki-1 renal carcinoma cells and shows that substandard doses of metformin potentiate rapamycin at 5 nM.
Figure 3:
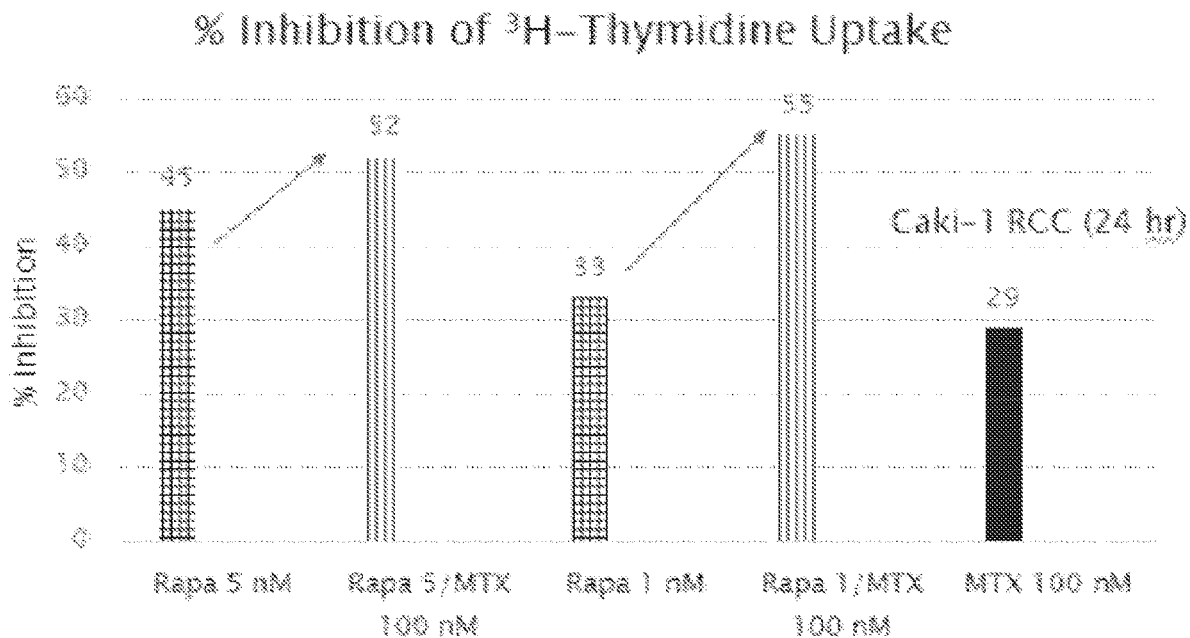
FIG. 3 is a bar graph depicting the percent inhibition of $^3$H-uptake of different doses of rapamycin and methotrexate alone or in combination in Caki-1 renal carcinoma cells and shows that standard doses of methotrexate potentiate low doses of rapamycin.
Figure 4:
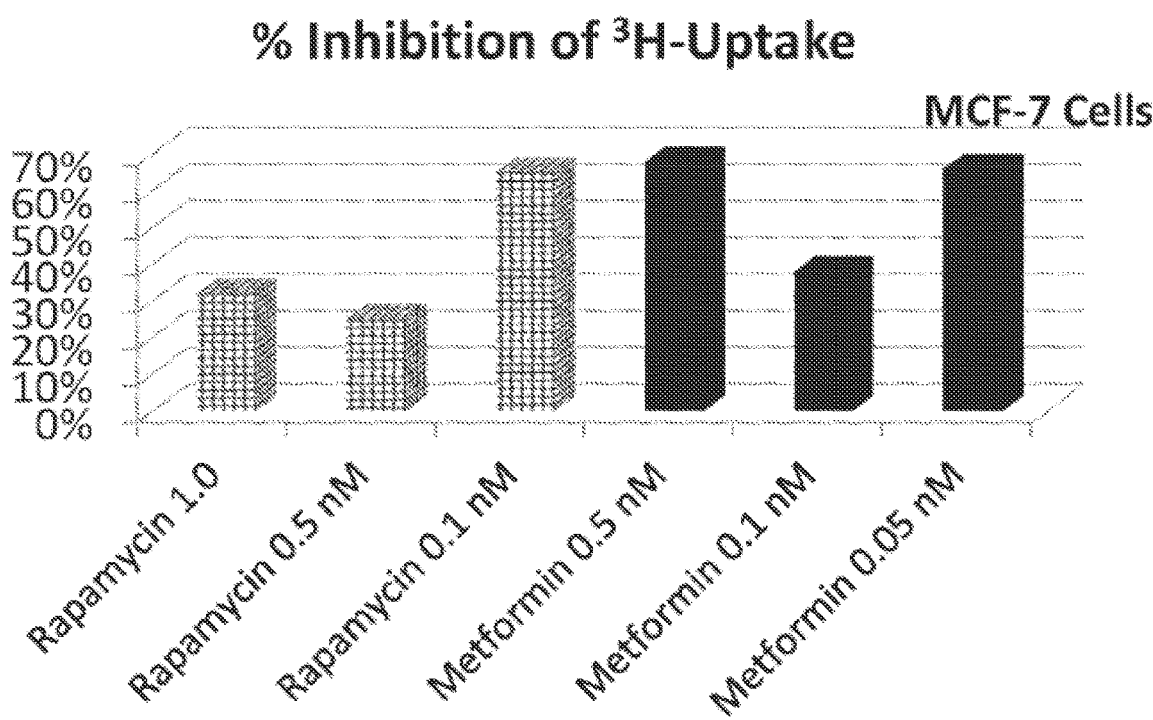
FIG. 4 is a bar graph depicting percent inhibition of 3H-uptake of different doses of rapamycin and metformin alone in MCF-7 breast cancer cells and shows that the effects of rapamycin and metformin alone are not dose-proportional.
Figure 5:
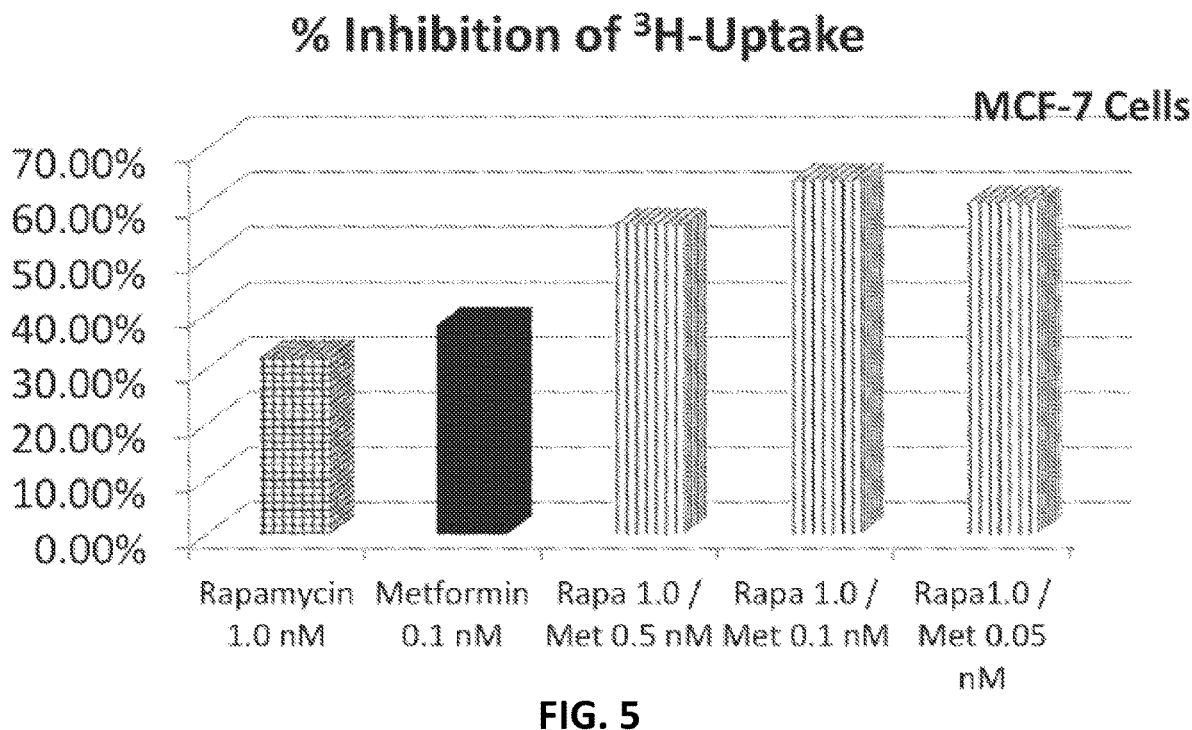
FIG. 5 is a bar graph depicting the percent inhibition of 3H-uptake of different doses of rapamycin and metformin alone or in combination in MCF-7 breast cancer cells and shows that low dose metformin combined with low dose rapamycin (1.0 nM) augments inhibition compared to rapamycin (1.0 nM) alone.
Figure 6:
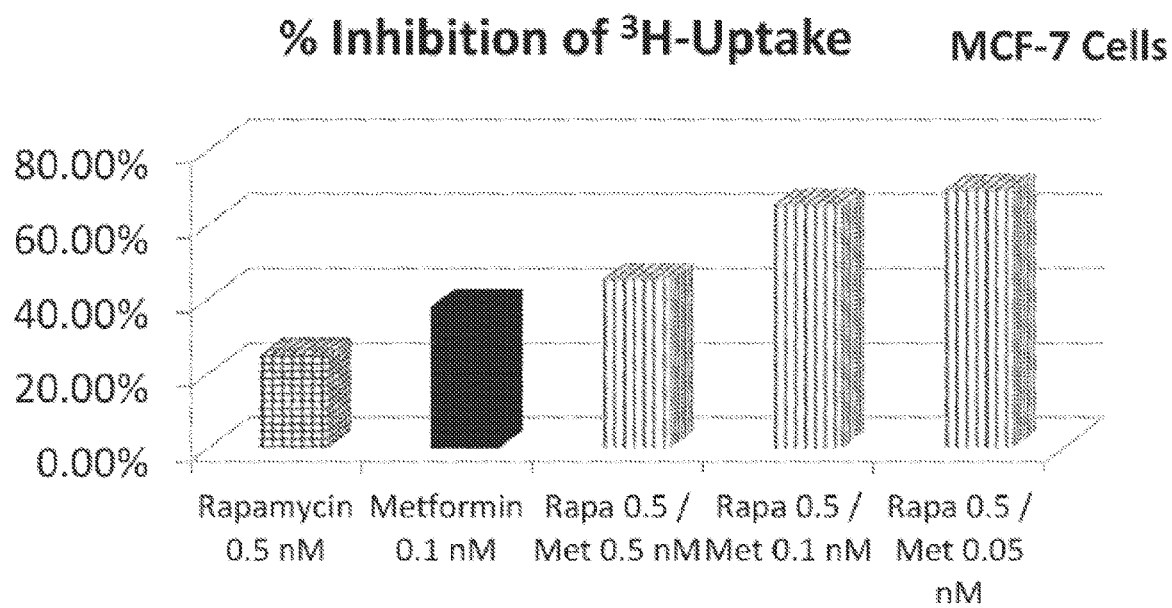
FIG. 6 is a bar graph depicting percent inhibition of 3H-uptake of different doses of rapamycin and metformin alone or in combination in MCF-7 breast cancer cells and shows that low dose metformin added to low dose rapamycin (0.5 nM) augments inhibition compared to rapamycin (0.5 nM) alone.
Figure 7:
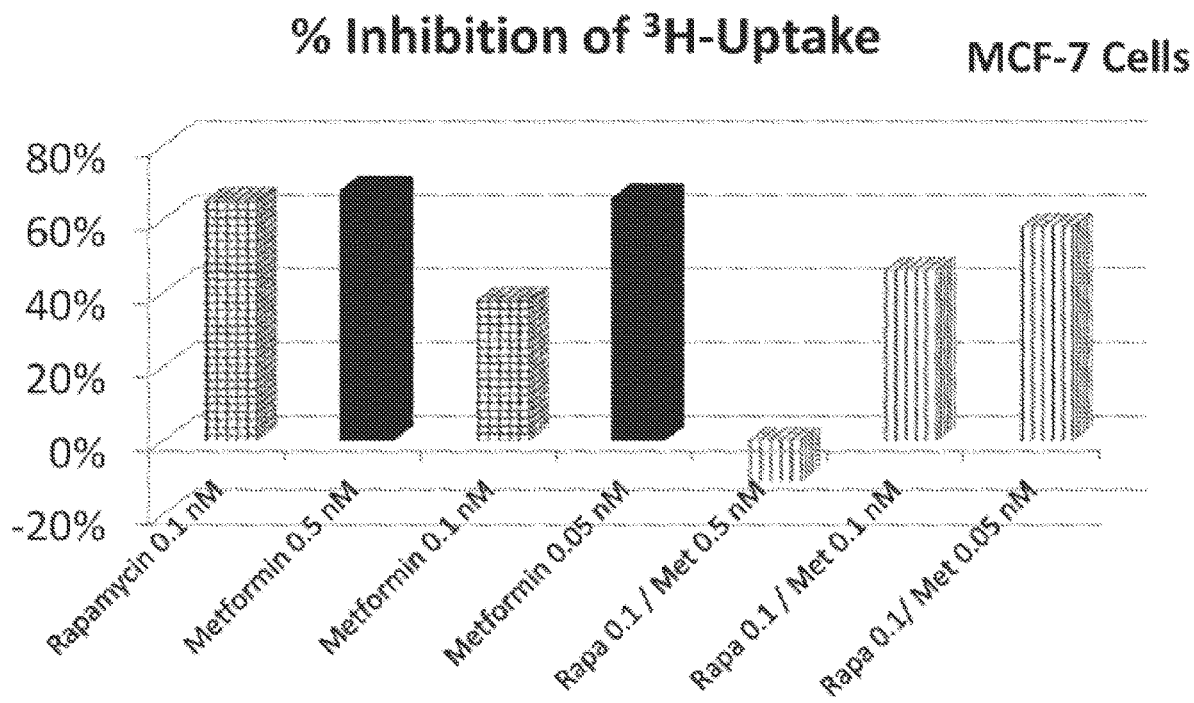
FIG. 7 is a bar graph depicting percent inhibition of 3H-uptake of different doses of rapamycin and metformin alone or in combination in MCF-7 breast cancer cells and shows that low dose metformin added to very low dose rapamycin (0.1 nM) adversely affects inhibition compared to rapamycin (0.1 nM) alone.

Rapamycin+metformin: 5 nM+5 nM, 5 nM+1 nM, 5 nM+0.5 nM, 1 nM+5 nM, 1 nM+1 nM, 1 nM+0.5 nM Control: 0.1% DMSO+media Results of the treatments are summarized in Table 2 and FIGS. 1-3.

TABLE 2

3H-Uptake in Human kidney clear cell carcinoma cell line Caki-I

| Treatment Article | Dosage | Cpm 1 | Cpm 2 | Cpm 3 | Average Cpm |
|---|---|---|---|---|---|
| Rapamycin | 10 nM | 9861 | 8987 | 8486 | 9111 |
| Rapamycin | 5 nM | 8771 | 7473 | 10030 | 8758 |
| Rapamycin | 1 nM | 10730 | 9692 | 11531 | 10651 |
| Metformin | 5 nM | 17424 | 13187 | 7921 | 15306 |
| Metformin | 1 nM | 18473 | 14784 | 15710 | 16322 |
| Metformin | 0.5 nM | 19450 | 16142 | 16208 | 17267 |
| Methotrexate | 100 nM | 10636 | 12192 | 4932 | 11414 |
| Control | Media + DMSO | 18333 | 13675 | 8579 | 16004 |
| Rapamycin + metformin | 5 nM + 5 nM | 6348 | 7191 | 6985 | 6841 |
| Rapamycin + metformin | 5 nM + 1 nM | 9023 | 6397 | 7401 | 7607 |
| Rapamycin + metformin | 5 nM + 0.5 nM | 8549 | 7403 | 4229 | 7976 |
| Rapamycin + metformin | 1 nM + 5 nM | 12571 | 13180 | 5759 | 12876 |
| Rapamycin + metformin | 1M + 1 nM | 3661 | 7519 | 10361 | 8940 |
| Rapamycin + metformin | 1 nM + 0.5 nM | 7749 | 10699 | 9373 | 9274 |
| Rapamycin + methotrexate | 5 nM + 100 nM | 7784 | 6636 | 8506 | 7642 |
| Rapamycin + methotrexate | 1 nM + 100 nM | 8471 | 5828 | 3434 | 7150 |

Cells treated with a combination of either rapamycin+metformin or rapamycin+methotrexate resulted in lower thymidine uptake compared to individual treatments
  with the notable exception of rapamycin+metformin at 1 nM+5 nM where the incorporation was slightly higher than rapamycin alone.

The results demonstrate a synergistic effect for combination treatments with the combination of rapamycin and metformin. Additivity was observed for the combination of rapamycin and methotrexate.

The results of Phase 2 showed that metformin alone had no effect on the inhibition of 3H-thymindine uptake at 5 nM, 1 nM, or 0.5 nM. When used in combination with rapamycin, however, metformin appeared to enhance the inhibitory response of rapamycin by approximately 30% relative to rapamycin alone. This was unexpected and is indicative of synergy.

Breast Cancer Human Cell Lines

Human breast adenocarcinoma cell line (MCF-7 (HTB-22) cells were exposed to various dosages of rapamycin, methotrexate, and metformin, either alone or in combination (see Tables below for dosages) to assess inhibition of DNA synthesis/replication. 0.1% DMSO, the test article solvent, in media was the control.

Possible augmentation of the inhibitory effects of rapamycin at very low, but clinically relevant doses was assessed by adding metformin to lower than standard doses of rapamycin to test its effect on inhibition of $^3$H-thymidine uptake.

The cells were passaged onto 24-well plates at a concentration of 50,000 cells/well, in total medium volume of 1 mL (DMEM+10% FBS+0.01 mg/mL insulin+antibiotics). The cells were then allowed to attach and were incubated from 24 hours before treatment. Cells were then treated, in triplicate, with various concentrations of treatment articles.

$^3$H-thymidine (1 mCi/mL) was diluted to 1 μCi in 5 μL of medium (DMEM+10% FBS+0.01 mg/mL insulin+antibiotics) and then added to each well at 18-hr post treatment.

Cells were then washed three times with 1 ML of DPBS at 24- or 48-hr post treatment to remove unincorporated $^3$H-thymidine. Each well of cells was then lysed in 0.5 mL of 0.5N NaOH+0.5% SDS. Lysate was then transferred to scintillation tubes containing 1 mL if scintillation fluid for counting (3 min/sample).

The cells were tested with the following treatment articles and evaluated at 24 hours post treatment:

Rapamycin: 1 nM, 0.5 nM, 0.1 nM

Metformin: 0.5 nM, 0.1 nM, 0.05 nM

Rapamycin+metformin: 0.1 nM+0.5 nM, 0.5 nM+0.5 nM, 0.1 nM+0.5 nM, 1 nM+0.1 nM, 0.5 nM+0.1 nM, 0.1 nM+0.1 nM, 1 nM+0.05 nM, 0.5 nM+0.05 nM, 0.1 nM+0.05 nM Table 3 and FIGS. 4-7 summarize the results.

TABLE 3

3H-Uptake in Human breast adenocarcinoma cell line (MCF-7)

| Treatment Article | Dosage | Cpm 1 | Cpm 2 | Cpm 3 | Average Cpm |
|---|---|---|---|---|---|
| Rapamycin | 1 nM | 3114 | 1220 | 2548 | 2294 |
| Rapamycin | 0.5 nM | 2537 | 2524 | 2567 | 2543 |
| Rapamycin | 0.1 nM | 1041 | 1516 | 986 | 1181 |
| Metformin | 0.5 nM | 1283 | 1048 | 921 | 1084 |
| Metformin | 0.1 nM | 2238 | 2595 | 1444 | 2092 |
| Metformin | 0.05 nM | 1267 | 1123 | 1041 | 1144 |
| Control | Media | 3722 | 3432 | 3013 | 3389 |
| Rapamycin + metformin | 1 nM + 0.5 nM | 1374 | 1590 | 1495 | 1486 |
| Rapamycin + metformin | 0.5 nM + 0.5 nM | 1568 | 1676 | 2320 | 1855 |
| Rapamycin + metformin | 0.1 nM + 0.5 nM | 3435 | 3917 | 3925 | 3759 |
| Rapamycin + metformin | 1 nM + 0.1 nM | 1149 | 862 | 1641 | 1217 |
| Rapamycin + metformin | 0.5 nM + 0.1 nM | 1547 | 1089 | 963 | 1200 |
| Rapamycin + metformin | 0.1 nM + 0.1 nM | 2403 | 1351 | 1762 | 1839 |
| Rapamycin + metformin | 1 nM + 0.05 nM | 1371 | 1369 | 1311 | 1350 |
| Rapamycin + metformin | 0.5 nM + 0.05 nM | 937 | 1291 | 909 | 1046 |
| Rapamycin + metformin | 0.1 nM + 0.05 nM | 1463 | 1771 | 1071 | 1435 |

The standard therapeutic serum trough levels of rapamycin considered to be clinically relevant for current uses is 5-20 ng/mL. The standard dose therapeutic serum Cmax for metformin is much higher at 1-2 microgram/mL. As can be seen in the above Table 3, the dosages used in these experiments for both rapamycin and metformin fall well below these levels.

At these lower doses of both rapamycin and metformin, the effects of rapamycin and metformin alone are not dose proportional.

Low dose metformin augments the inhibitory effect of rapamycin (1.0 nM) vs rapamycin alone. The lease effective does of metformin (0.1 nM) more than doubles the inhibitory effect of rapamycin at 1.0 nM (64% vs. 32%) and rapamycin at 0.5 nM (65% vs. 25%). (See FIGS. 5 and 6.)

Figure 8:
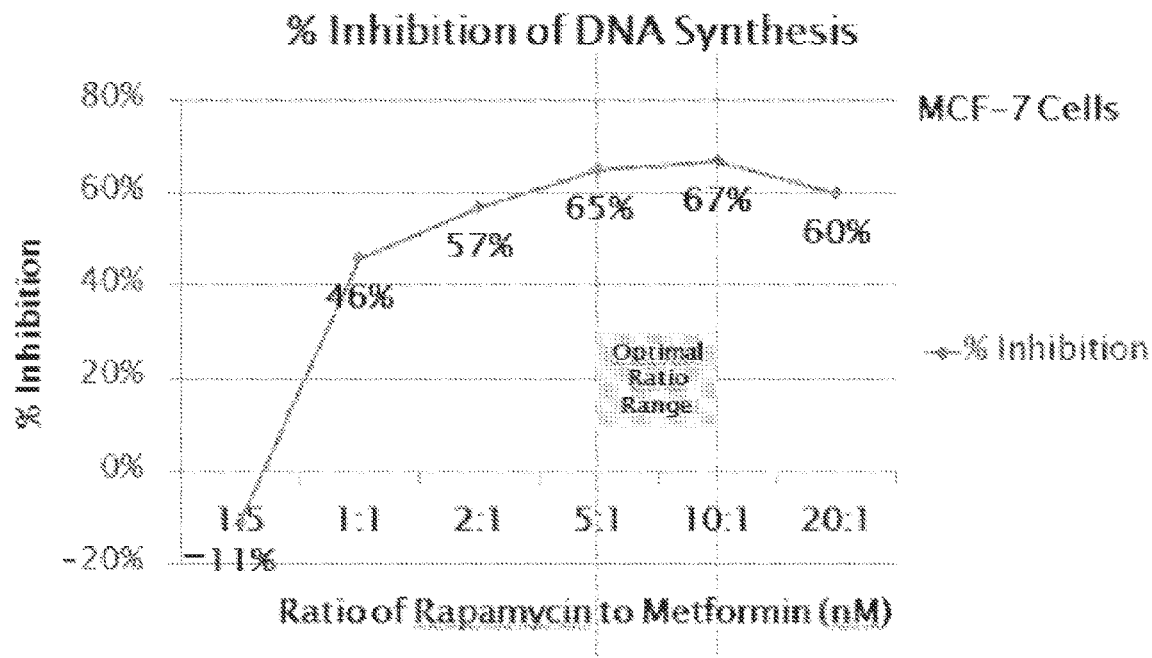
FIG. 8 is a graph comparing the percent inhibition of $^3$H-uptake and the molar ratio of rapamycin to metformin in MCF-7 breast cancer cells. The optimal molar ratio range for inhibition of $^3$H-uptake is between 5:1 and 10:1.

FIGS. 4-7 depict bar graphs representing the percent inhibition of $^3$H-uptake for each concentration. The data indicate that when the ratio of rapamycin to metformin is too low (e.g., less than 5:1), the combination loses efficacy. (See FIGS. 7 and 8). Thus, the percent inhibition of $^3$H-thymidine uptake (e.g., DNA synthesis) is ratio dependent, not dose-dependent. (Table 4.)

TABLE 4

| Comparison of Efficacy of Rapamycin to Metformin Ratios | | | | | | |
|---|---|---|---|---|---|---|
| Ration of Rapamycin to Metformin | 1:5 | 1:1 | 2:1 | 5:1 | 10:1 | 20:1 |
| Rapa (nM)/Metformin (nM) | 0.1/0.5 | 0.1/0.1 | 0.1/0.05 | 0.5/0.1 | 0.5/0.05 | 1.0/0.5 |
| % Inhibition | −11%* | 46% | 58% | 65% | 69% | 60% |
| Rapa (nM)/Metformin (nM) | | | 1.0/0.5 | | 1.0/0.1 | |
| % Inhibition | | | 56% | | 64% | |

*An inverted ratio of 1:5 was antagonistic.

While the invention has been described with reference to various exemplary embodiments, it will be appreciated that modifications may occur to those skilled in the art, and the present application is intended to cover such modifications and inventions as fall within the spirit of the invention.

What is claimed is:

1. A method of treating a neurodegenerative disease or disorder comprising administering an effective amount of a composition comprising a combination of rapamycin and metformin to a subject, wherein the molar ratio of rapamycin to metformin is in the range of about 20:1 to about 1:1.

2. The method of claim 1, wherein the molar ratio of rapamycin to metformin is in the range of about 15:1 to about 3:1.

3. The method of claim 1, wherein the molar ratio of rapamycin to metformin is in the range of about 10:1 to about 4:1.

4. The method of claim 1, wherein the molar ratio of rapamycin to metformin is about 5:1 to about 3:1.

5. The method of claim 1, wherein the molar ratio of rapamycin to metformin is about 5:1 to about 4:1.

6. The method of claim 1, wherein the neurodegenerative disease or disorder is associated with mTORC1 hyperactivation, or an acquired neurodegenerative disease or disorder.

7. The method of claim 6, wherein the neurodegenerative disease or disorder is Alzheimer's disease (AD), Parkinson's disease, Amyotrophic Lateral Sclerosis (ALS), Frontotemporal Dementia (FTD), Dementia with Lewy Bodies, Huntington's disease, amyloid associated vasculopathies, traumatic brain injury-related disease, or a tauopathy.

8. The method of claim 6, wherein the neurodegenerative disease or disorder is associated with mTORC1 hyperactivation and is Alzheimer's disease, ALS, tauopathies, Parkinson's Disease, FTD, or Tuberous Sclerosis Complex, and Seizure Disorders.

9. The method of claim 1, wherein the composition is formulated for oral administration.

10. The method of claim 1, wherein the composition is formulated for topical administration.

11. The method of claim 1, wherein the composition is formulated for parenteral administration.

12. The method of claim 9, wherein the composition comprises a nanoparticle encapsulating at least the rapamycin, the metformin, or the combination of rapamycin and metformin.

13. A method of treating a neurodegenerative disease or disorder mediated by mTORC1 activation comprising administering an effective amount of a composition comprising a combination of rapamycin and metformin to a subject, wherein the molar ratio of rapamycin to metformin is in the range of about 20:1 to about 1:1.

14. The method of claim 13, wherein the molar ratio of rapamycin to metformin is in the range of about 10:1 to about 4:1.

15. The method of claim 14, wherein the composition comprises a nanoparticle encapsulating at least the rapamycin, the metformin, or the combination of rapamycin and metformin.

16. The method of claim 13, wherein the neurodegenerative disease or disorder is AD.

17. The method of claim 13, wherein the neurodegenerative disease or disorder occurs either sporadically or as part of TSC.

* * * * *

UNITED STATES PATENT AND TRADEMARK OFFICE
CERTIFICATE OF CORRECTION

| | | |
|---|---|---|
| PATENT NO. | : 12,409,170 B2 | Page 1 of 1 |
| APPLICATION NO. | : 18/394155 | |
| DATED | : September 9, 2025 | |
| INVENTOR(S) | : Jeffrey M. Melin | |

It is certified that error appears in the above-identified patent and that said Letters Patent is hereby corrected as shown below:

On the Title Page

In Item (73) Assignee, delete "IMM Licensing LLC, Meadowbrook, PA (US)" and insert
-- JMM Licensing LLC, Meadowbrook, PA (US) --.

Signed and Sealed this
Eleventh Day of November, 2025

John A. Squires
*Director of the United States Patent and Trademark Office*